United States Patent
Lim

(10) Patent No.: US 10,088,709 B2
(45) Date of Patent: Oct. 2, 2018

(54) ALIGNMENT LAYER COMPOSITION, LIQUID CRYSTAL DISPLAY INCLUDING THE SAME, AND METHOD OF MANUFACTURING THE LIQUID CRYSTAL DISPLAY

(71) Applicant: Samsung Display Co. Ltd., Yongin, Gyeonggi-do (KR)

(72) Inventor: Ho Lim, Suwon-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 268 days.

(21) Appl. No.: 15/072,995

(22) Filed: Mar. 17, 2016

(65) Prior Publication Data

US 2017/0075173 A1 Mar. 16, 2017

(30) Foreign Application Priority Data

Sep. 15, 2015 (KR) .................. 10-2015-0130017

(51) Int. Cl.

| G02F 1/1337 | (2006.01) |
|---|---|
| G02F 1/1341 | (2006.01) |
| C07D 251/34 | (2006.01) |
| C07D 251/30 | (2006.01) |
| C09K 19/56 | (2006.01) |
| C07C 69/54 | (2006.01) |

(52) U.S. Cl.
CPC ........ *G02F 1/133788* (2013.01); *C07C 69/54* (2013.01); *C07D 251/30* (2013.01); *C07D 251/34* (2013.01); *C09K 19/56* (2013.01); *G02F 1/1341* (2013.01); *G02F 1/133711* (2013.01); *G02F 2001/133742* (2013.01); *Y10T 428/10* (2015.01); *Y10T 428/1005* (2015.01)

(58) Field of Classification Search
CPC ........... G02F 1/133788; G02F 1/13378; G02F 1/133711; G02F 1/1341; G02F 1/133365; G02F 2001/133749; C09K 19/56; C09K 2019/548; C09K 2019/3422; C07D 69/602; C07D 251/30; C07D 251/34; C07D 69/604; Y10T 428/10; Y10T 428/1005; Y10T 428/1036
USPC ........... 428/1.1, 1.2, 1.3; 349/123, 127, 182, 349/191; 252/299.61, 299.62, 299.66
See application file for complete search history.

(56) References Cited

U.S. PATENT DOCUMENTS

2013/0287970 A1* 10/2013 Zhong .................. C09K 19/062
428/1.1

FOREIGN PATENT DOCUMENTS

KR 1020170019544 A 2/2017

* cited by examiner

*Primary Examiner* — Ruiyun Zhang
(74) *Attorney, Agent, or Firm* — Cantor Colburn LLP

(57) ABSTRACT

An alignment layer composition includes a reactive monomer of Formula 1 below.

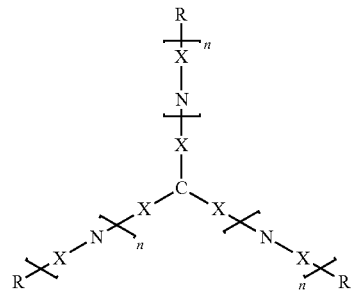

Formula 1

15 Claims, 9 Drawing Sheets

ALIGNMENT LAYER COMPOSITION, LIQUID CRYSTAL DISPLAY INCLUDING THE SAME, AND METHOD OF MANUFACTURING THE LIQUID CRYSTAL DISPLAY

This application claims priority to Korean Patent Application No. 10-2015-0130017, filed on Sep. 15, 2015, and all the benefits accruing therefrom under 35 U.S.C. § 119, the content of which in its entirety is herein incorporated by reference.

BACKGROUND

1. Field of the Invention

The present invention relates to an alignment layer composition, a liquid crystal display (LCD) including the same, and a method of manufacturing the LCD.

2. Description of the Related Art

Liquid crystal displays (LCDs) are one of the most widely used types of flat panel displays. Generally, an LCD includes a pair of substrates having field generating electrodes, such as pixel electrodes and a common electrode, and a liquid crystal layer interposed between the two substrates.

In an LCD, voltages are applied to field generating electrodes to generate an electric field in the liquid crystal layer. Accordingly, the alignment of liquid crystal molecules within the liquid crystal layer is determined by the electric field, and polarization of incident light is controlled. As a result, a desired image is displayed on the LCD.

SUMMARY

Aspects of the present invention provide an alignment layer composition which can increase the vertical alignment of liquid crystals and cause the liquid crystals to pretilt easily.

Aspects of the present invention also provide a liquid crystal display (LCD) including the alignment layer composition and a method of manufacturing the LCD.

According to an exemplary embodiment, an alignment layer composition includes a reactive monomer represented by Formula 1 below:

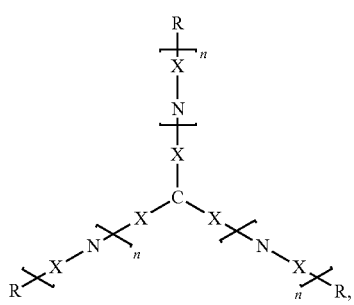

Formula 1 where in Formula 1 n is 0 or 1; C is

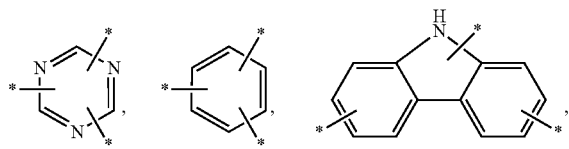

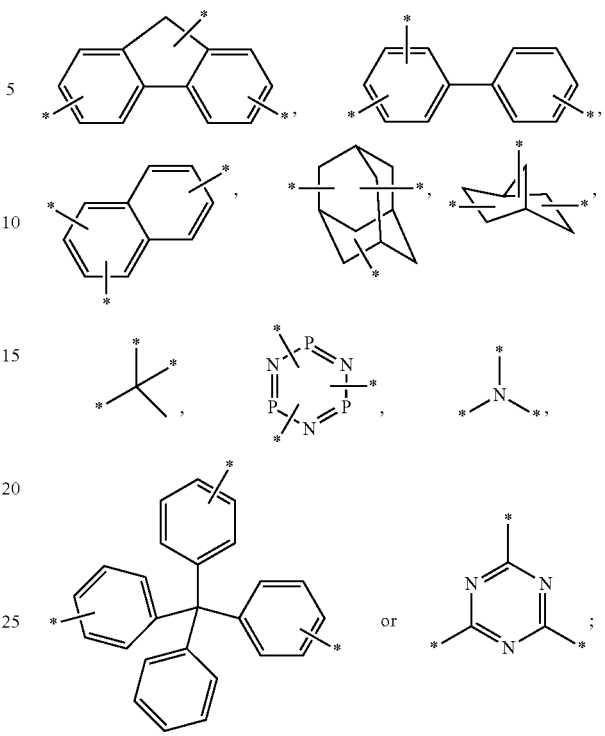

each X is independently ★—O—★,

or a bond; each N is independently

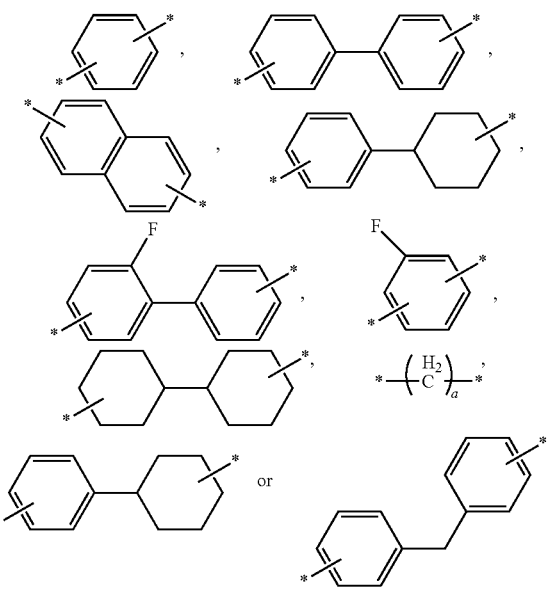

wherein a is a natural number of 1 to 20; and each R is independently

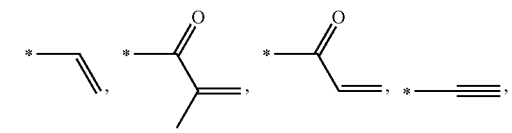

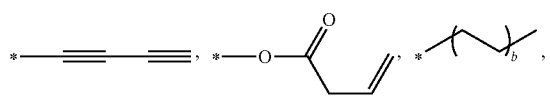

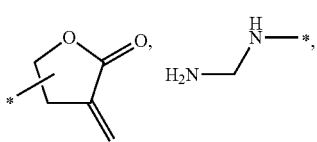

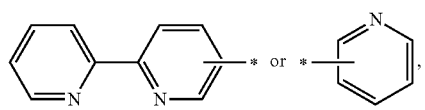

wherein b is a natural number of 1 to 20

In an exemplary embodiment, the reactive monomer of Formula 1 may be represented by Formula 2 below:

Formula 2

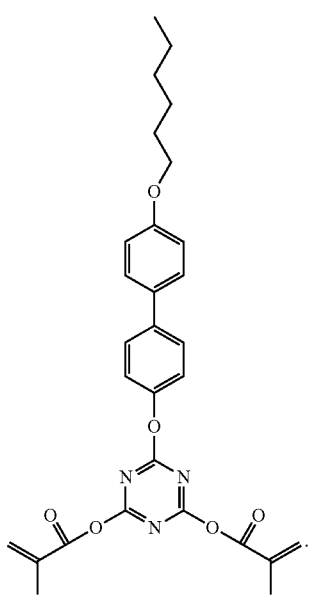

In an exemplary embodiment, the reactive monomer of Formula 1 may be represented by Formula 3 below:

Formula 3

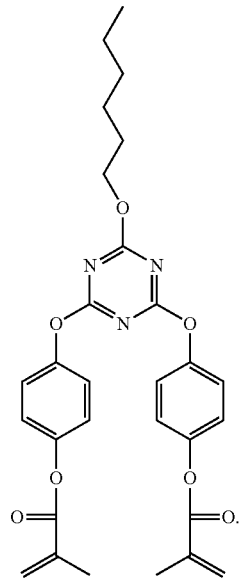

In an exemplary embodiment, the reactive monomer of Formula 1 may be represented by Formula 4 below:

Formula 4

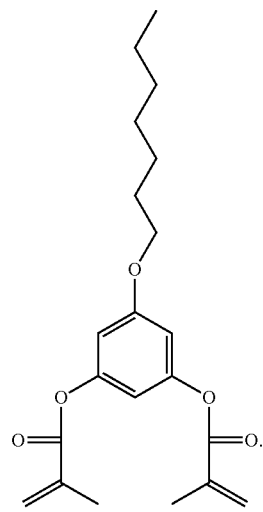

In an exemplary embodiment, the reactive monomer of Formula 1 may include a mixture of reactive monomer A in which each R is independently

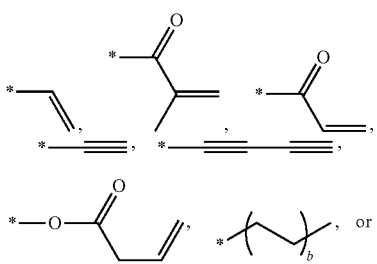

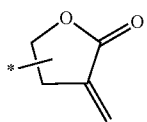

and reactive monomer B in which each R is independently

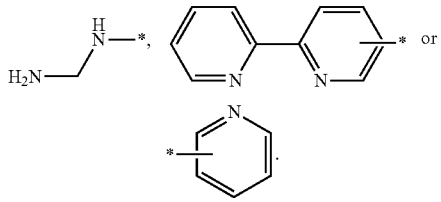

In an exemplary embodiment, for the reactive monomer of Formula 1, any one or two of R may be

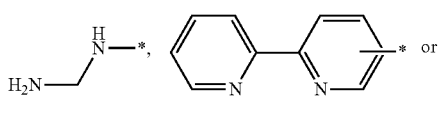

and the other one or two of R may be

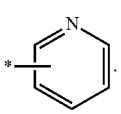

According to an exemplary embodiment, a liquid crystal display (LCD) includes a first substrate, a second substrate facing the first substrate, a liquid crystal layer disposed between the first substrate and the second substrate, a first liquid crystal alignment layer disposed between the liquid crystal layer and the first substrate, and a second liquid crystal alignment layer which is disposed between the liquid crystal layer and the second substrate, wherein at least one of the first liquid crystal alignment layer and the second liquid crystal alignment layer comprises a reactive monomer represented by Formula 1 below:

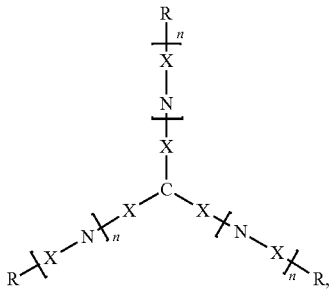

Formula 1 wherein in Formula 1 n is 0 or 1; C is

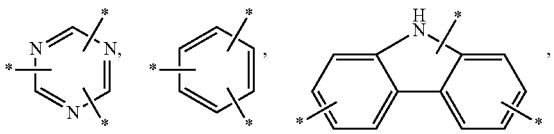

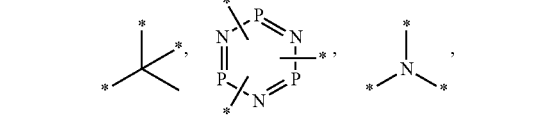

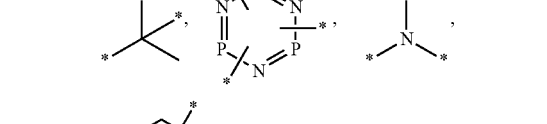

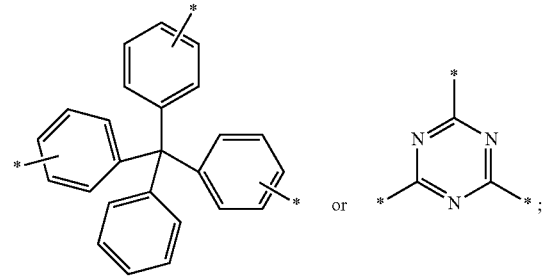

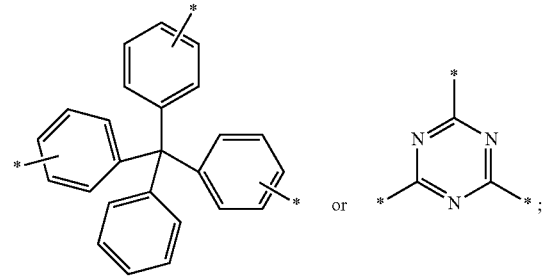

each X is independently ★—O—★,

or a bond; each N is independently

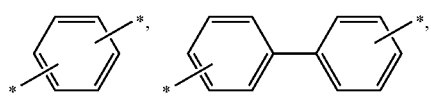

-continued

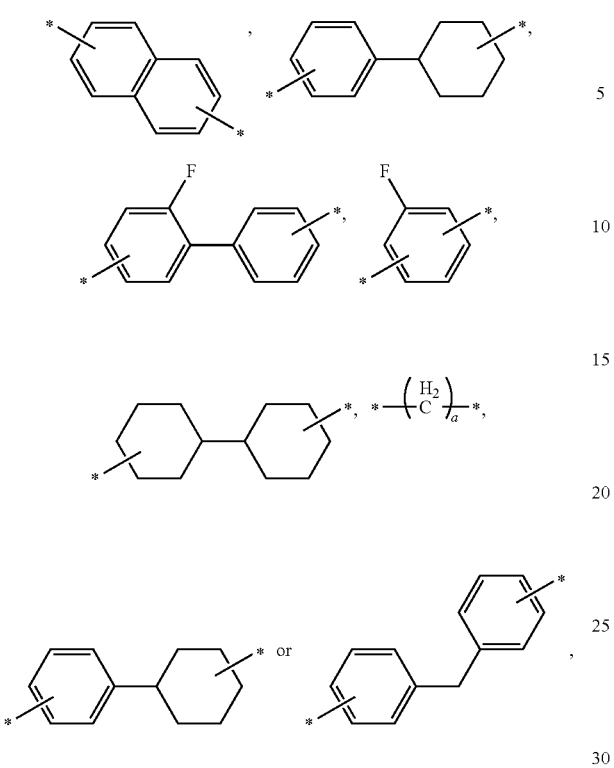

wherein a is a natural number of 1 to 20; and each R is independently wherein b is a natural number of 1 to 20.

In an exemplary embodiment, the reactive monomer of Formula 1 may be represented by Formula 2 below:

Formula 2

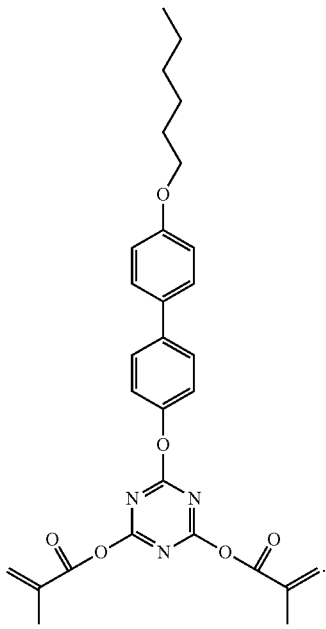

In an exemplary embodiment, the reactive monomer of Formula 1 may be represented by Formula 3 below:

Formula 3

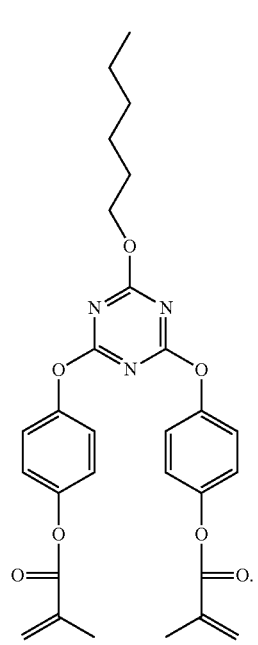

In an exemplary embodiment, the reactive monomer of Formula 1 may be represented by Formula 4 below:

Formula 4

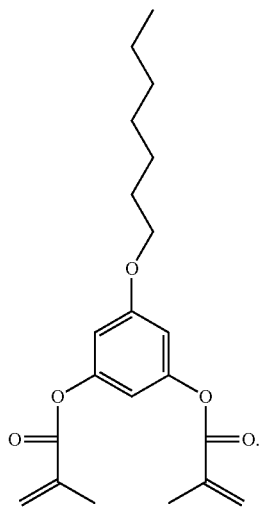

In an exemplary embodiment, the reactive monomer of Formula 1 includes a mixture of reactive monomer A in which each R may be independently

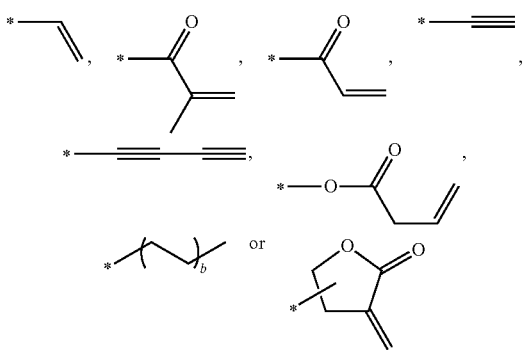

and reactive monomer B in which each R is independently

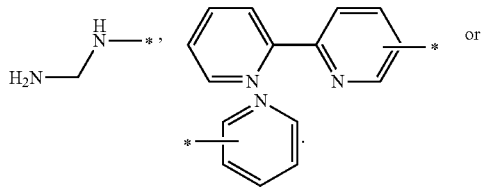

In an exemplary embodiment, the reactive monomer of Formula 1, any one or two of R may be

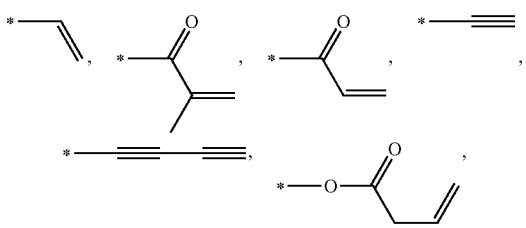

-continued

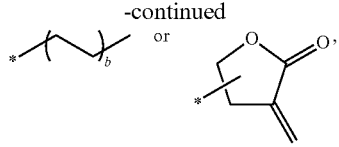

and the other one or two of R is

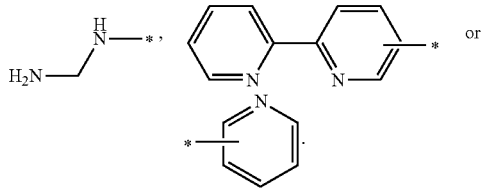

In an exemplary embodiment, both the first liquid crystal alignment layer and the second liquid crystal alignment layer may include the reactive monomer of Formula 1.

According to an exemplary embodiment, a method of manufacturing an LCD includes preparing a first substrate and a second substrate facing each other, injecting a liquid crystal composition into a space between the first substrate and the second substrate, irradiating UV light toward at least one of the first substrate and the second substrate in the absence of an electric field, and irradiating UV light toward at least one of the first substrate and the second substrate in the presence of the electric field, wherein the liquid crystal composition comprises a reactive monomer represented by Formula 1 below:

Formula 1

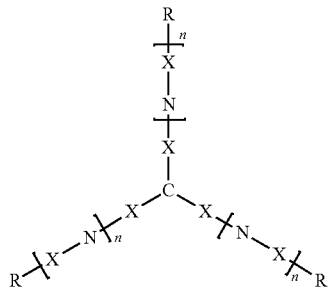

wherein in Formula 1 n is 0 or 1; C is

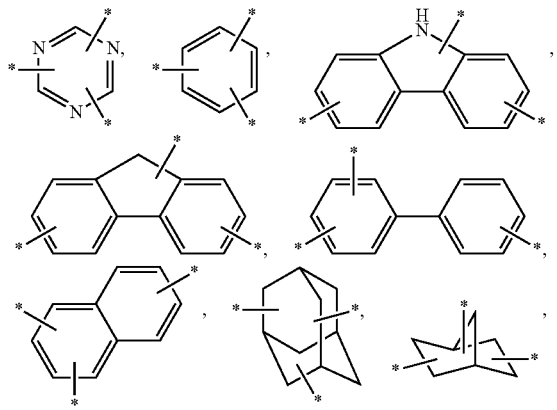

-continued

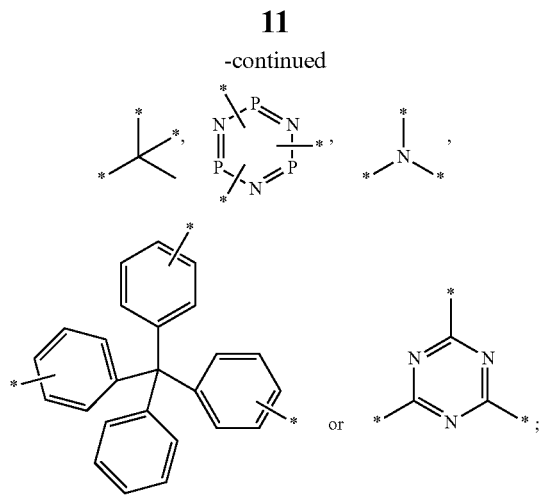

each X is independently ★—O—★,

or a bond; each N is independently

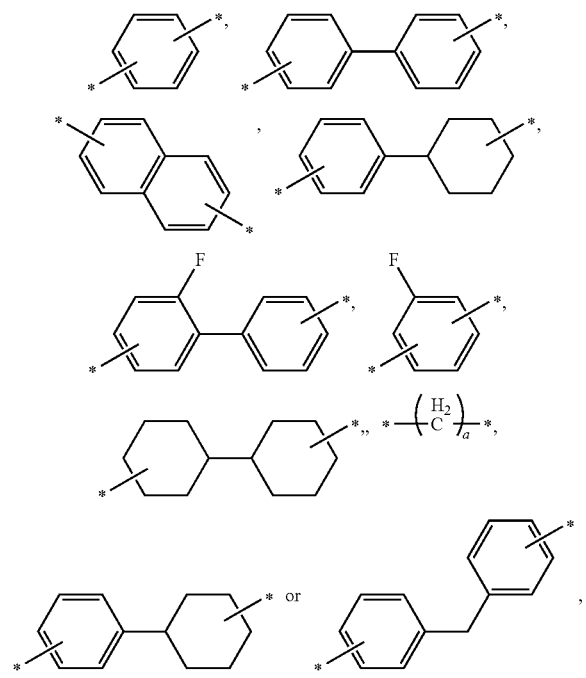

wherein a is a natural number from 1 to 20; and each R is independently

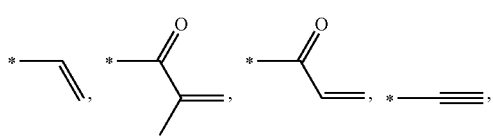

-continued

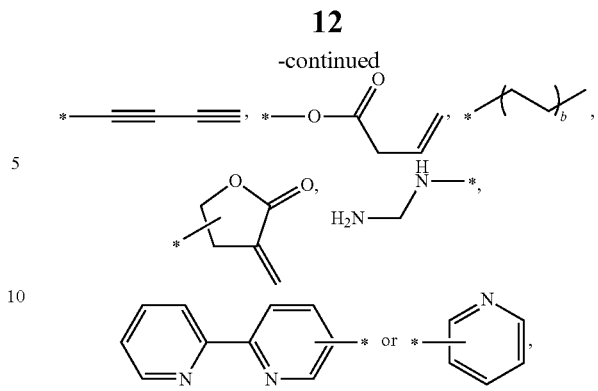

wherein b is a natural number of 1 to 20.

In an exemplary embodiment, the irradiating of the UV light in the absence of the electric field may polymerize the reactive monomer to form a first liquid crystal alignment layer on a surface of the first substrate which faces the second substrate and a second liquid crystal alignment layer on a surface of the second substrate which faces the first substrate.

In an exemplary embodiment, the injecting of the liquid crystal composition further includes forming a liquid crystal layer including first liquid crystal molecules aligned on a surface of the first liquid crystal alignment layer and second liquid crystal molecules aligned on a surface of the second liquid crystal alignment layer, and the irradiating of the UV light in the absence of the electric field aligns the first liquid crystal molecules and the second liquid crystal molecules in a direction perpendicular to the first substrate or the second substrate, wherein the first liquid crystal molecules and the second liquid crystal molecules have negative dielectric anisotropy.

In an exemplary embodiment, the method further includes removing the electric field after the irradiating of the UV light in the presence of the electric field, wherein the first liquid crystal molecules and the second liquid crystal molecules may be aligned at an angle relative to the first substrate or the second substrate after the irradiating of the UV light in the presence of the electric field.

In an exemplary embodiment, at least one of the first liquid crystal alignment layer and the second liquid crystal alignment layer may be formed as a single layer of the polymerized reactive monomer of Formula 1.

In an exemplary embodiment, the reactive monomer of Formula 1, any one or two of R may be

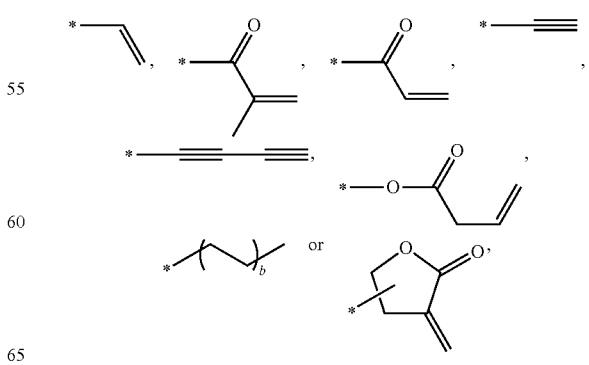

and the other one or two of R may be

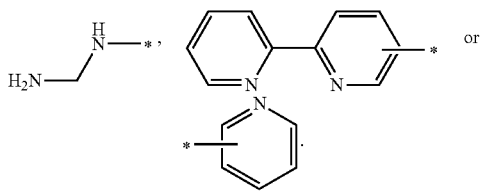

In an exemplary embodiment, the method of manufacturing an LCD may further comprise irradiating UV light again after the irradiating of the UV light in the presence of the electric field.

The effects according to the present invention are not limited to the contents as exemplified above, but further various effects are included in the description.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION

Figure 1:
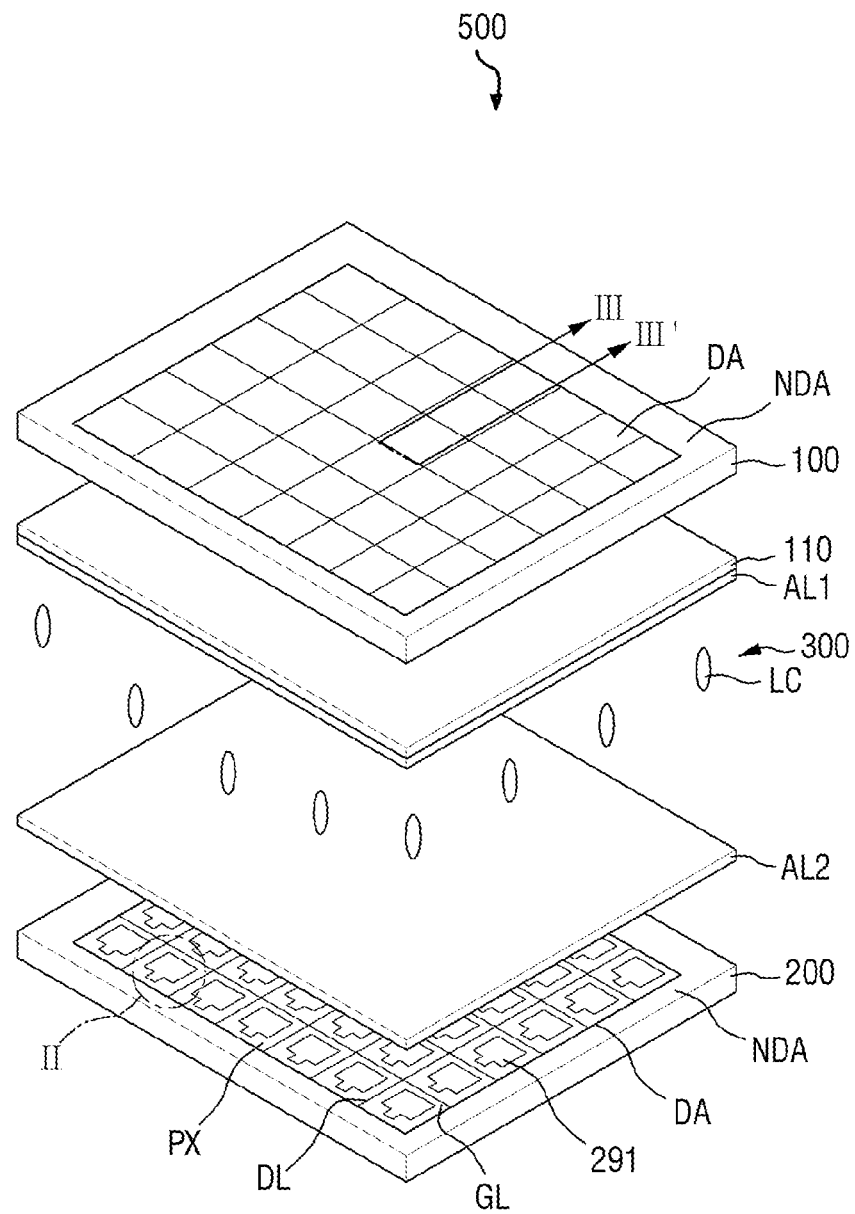
FIG. 1 is a schematic exploded perspective view of an exemplary embodiment of a liquid crystal display (LCD)

The aspects and features of the present invention and methods for achieving the aspects and features will be apparent by referring to the embodiments to be described in detail with reference to the accompanying drawings. However, the present invention is not limited to the embodiments disclosed hereinafter, but can be implemented in diverse forms. The matters defined in the description, such as the detailed construction and elements, are nothing but specific details provided to assist those of ordinary skill in the art in a comprehensive understanding of the invention, and the present invention is only defined within the scope of the appended claims. In the entire description of the present invention, the same reference numerals are used for the same elements across various figures. In the drawings, sizes and relative sizes of layers and areas may be exaggerated for clarity in explanation.

In the drawings, the thickness of layers and regions are exaggerated for clarity. It will be understood that when an element or layer is referred to as being "on," "connected to," or "coupled to" another element or layer, the element or layer can be directly on, connected or coupled to another element or layer or intervening elements or layers. In contrast, when an element is referred to as being "directly on," "directly connected to" or "directly coupled to" another element or layer, there are no intervening elements or layers present. As used herein, connected may refer to elements being physically, electrically and/or fluidly connected to each other.

Although the terms "first, second, third, and so forth" are used to describe diverse constituent elements, such constituent elements are not limited by the terms. The terms are used only to discriminate a constituent element from another constituent element. Accordingly, in the following description, a first constituent element may be a second constituent element.

Spatially relative terms, such as "bottom," "below," "lower," "under," "above," "upper," "top" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "beneath" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. "Or" means "and/or." It will be further understood that the terms "comprises," "comprising," "includes" and/or "including," when used in this specification, specify the presence of stated features, integers, operations, elements, and/or components, but do not preclude the presence or addition of one or more other features, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, exemplary embodiments will be described in detail with reference to the accompanying drawings.

An alignment layer composition according to an embodiment of the present invention includes a reactive monomer represented by Formula 1 below:

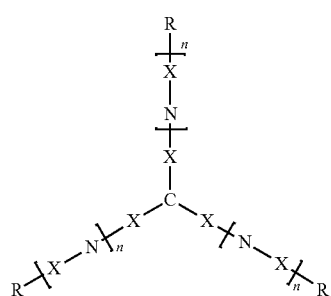

Formula 1 where in Formula 1 n is 0 or 1; C is

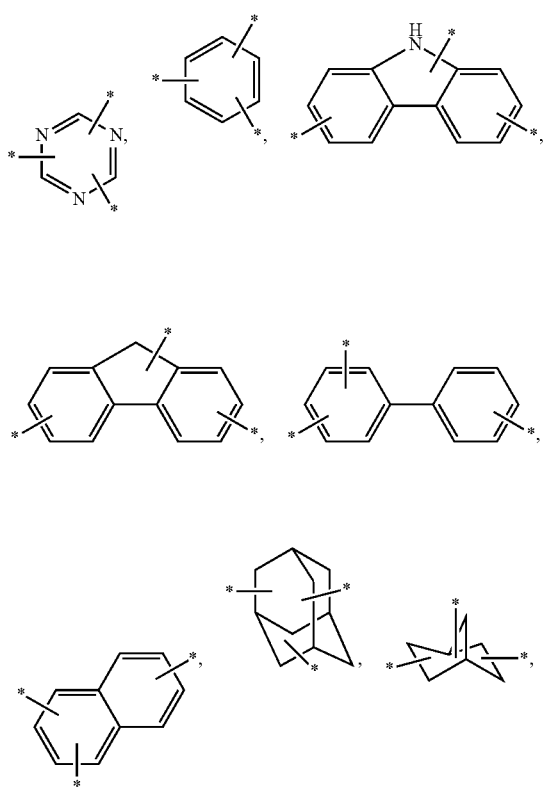

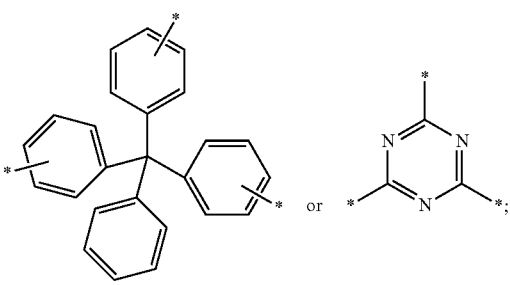

each X is independently ★—O—★,

or a bond; each N is independently

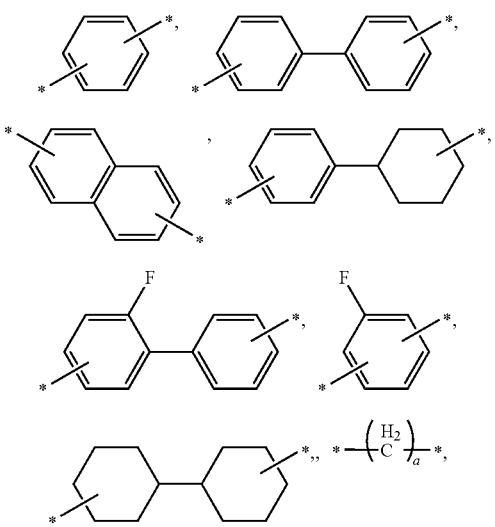

wherein a is a natural number of 1 to 20; and each R is independently

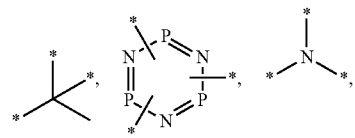

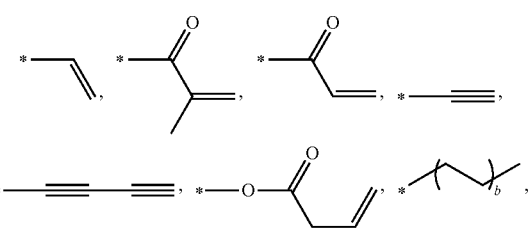

-continued

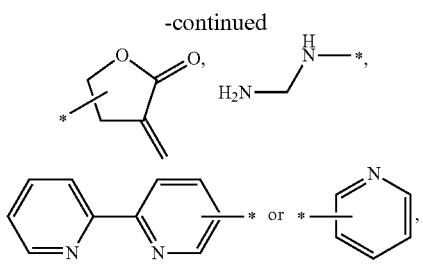

wherein b is a natural number of 1 to 20.

Using the reactive monomer of Formula 1, a first liquid crystal alignment layer and a second liquid crystal alignment layer may be formed on a surface of a pixel electrode and a surface of a common electrode which face each other in a liquid crystal display (LCD). The reactive monomer may be mixed with liquid crystals and introduced accordingly into the LCD. Therefore, a separate process of forming an alignment layer can be omitted.

That is, in a conventional LCD, a liquid crystal alignment layer is formed by coating an alignment layer on a pixel electrode or on a common electrode, that is, on surfaces of the pixel electrode and the common electrode which face each other, and then drying the alignment layer. However, when the alignment layer composition described herein is utilized, the separate process of forming an alignment layer is not necessary. Instead, a liquid crystal alignment layer can be formed by injecting a liquid crystal composition including the alignment layer composition and performing a subsequent process. That is, the liquid crystal alignment layer can be formed more easily.

The reactive monomer of Formula 1 may include a mixture of reactive monomer A in which the R is

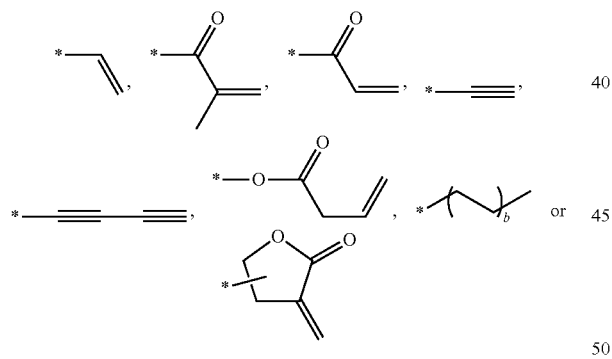

and reactive monomer B in which the R is

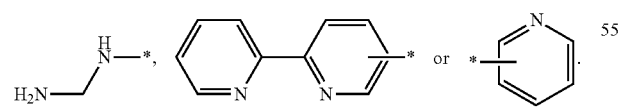

That is, the reactive monomer of Formula 1 includes two or more types of reactive monomers to form a liquid crystal alignment layer through the polymerization of the two or more types of reactive monomers. A liquid crystal alignment layer including a polymerization product of two or more types of monomers causes liquid crystal molecules located on the surface of the liquid crystal alignment layer to be aligned vertically and to pretilt.

In addition, the reactive monomer of Formula 1 may be a single reactive monomer in which any one or two of R is

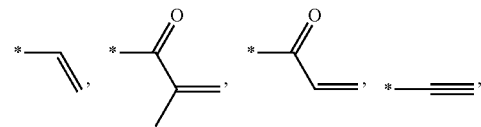

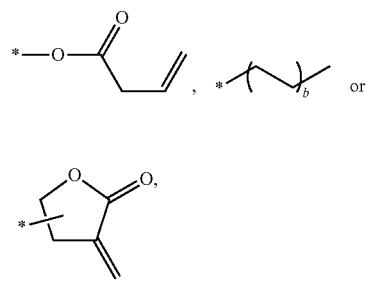

and the other one or two of R is

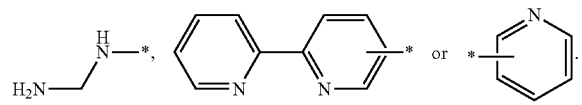

The reactive monomer of Formula 1 can be represented by, for example, Formulas 2 through 4 below:

Formula 2

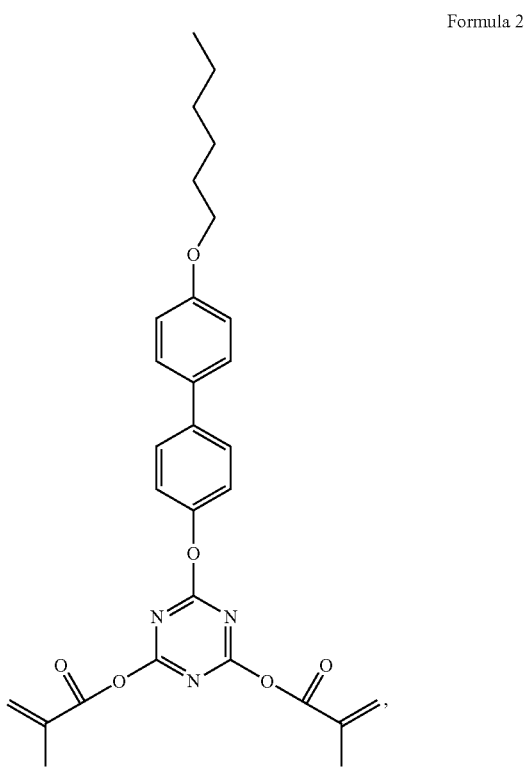

-continued

Formula 3

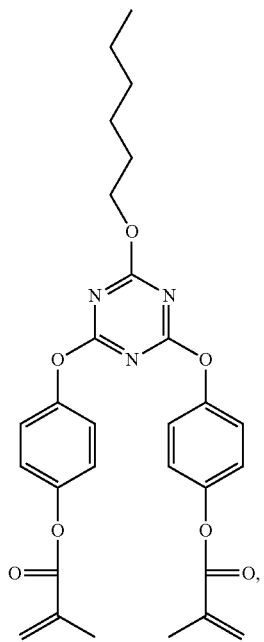

Formula 4 and the common electrode 110 and may be a patterned electrode having a slit pattern.

The liquid crystal layer 300 may be disposed between the common electrode 110 and the pixel electrode 291. The liquid crystal layer 300 may include liquid crystal molecules LC having negative dielectric anisotropy. A first liquid crystal alignment layer AL1 may be disposed between the common electrode 110 and the liquid crystal layer 300, and a second liquid crystal alignment layer AL2 may be disposed between the pixel electrode 291 and the liquid crystal layer 300.

The second substrate 200 may be a thin-film transistor (TFT) substrate. A plurality of gate lines GL extending in a first direction and a plurality of data lines DL extending in a second direction perpendicular to the first direction may be formed in the display area DA of the second substrate 200. The pixel electrode 291 may be disposed in each of pixels PX defined by the gate lines GL and the data lines DL.

The pixel electrode 291 may include subpixel electrodes 291-1 and 291-2 separated from each other. For example, each of the subpixel electrodes 291-1 and 291-2 may have a quadrilateral shape. Each of the subpixel electrodes 291-1 and 291-2 may be a patterned electrode having a slit pattern. Specifically, the slit pattern may consist of a stem SC and slits DC disposed between branches BC extending from the stem SC. The stem SC may be shaped like a cross (+), and the branches BC may extend radially from the cross-shaped stem SC in a direction at an angle of approximately 45 degrees to the stem SC.

A gate line GL may include gate electrodes 224-1 and 224-2 which protrude from the gate line GL in the second direction toward the pixel electrode 291. A plurality of data lines DL may include source electrodes 273-1 and 273-2 and drain electrodes 275-1 and 275-2. The source electrodes 273-1 and 273-2 may extend from the data lines DL in a "U" shape. The drain electrodes 275-1 and 275-2 may be separated from the source electrodes 273-1 and 273-2.

The pixel electrode 291 may receive a data voltage through a TFT, which is a switching device. The gate electrodes 224-1 and 224-2 which are control terminals of TFTs may be electrically connected to the gate line GL, the source electrodes 273-1 and 273-2 which are input terminals of the TFTs may be electrically connected to the data lines DL via contact holes 285-1, 285-2, 285-3, and 285-4, and the drain electrodes 275-1 and 275-2 which are output terminals of the TFTs may be electrically connected to the pixel electrode 291.

The pixel electrode 291 may generate an electric field together with the common electrode 110, thereby controlling the alignment direction of the liquid crystal molecules LC of the liquid crystal layer 300 interposed therebetween. The pixel electrode 291 may control the alignment direction of first liquid crystal molecules LC1 and the alignment direction of second liquid crystal molecules LC2 by distorting the electric field.

The TFT substrate may include a stack of a base substrate (not illustrated) which is made of glass or polymer, the gate electrodes 224-1 and 224-2, a gate insulating layer (not illustrated), a semiconductor layer (not illustrated), an ohmic contact layer (not illustrated), the source electrodes 273-1 and 273-2, the drain electrodes 275-1 and 275-2, a passivation layer (not illustrated), and an organic layer (not illustrated), etc.

Figure 2:
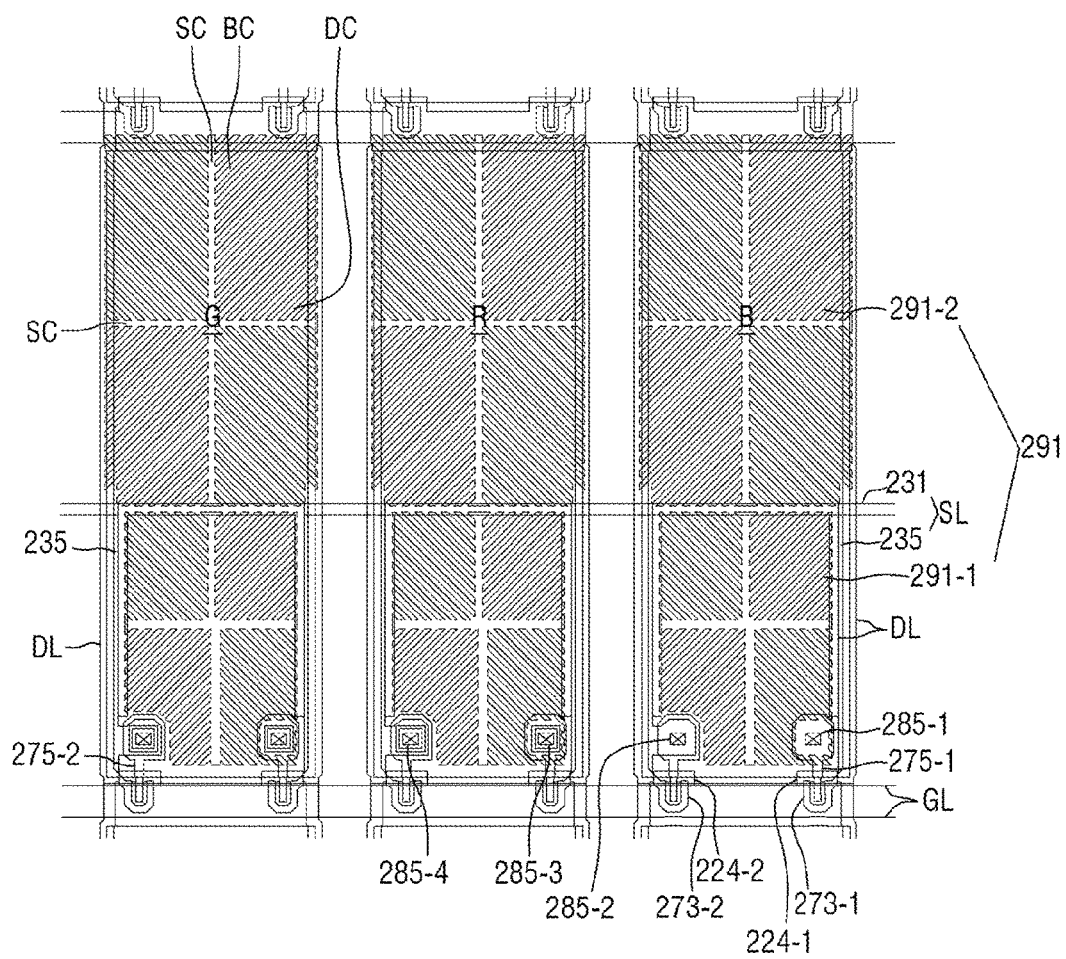
FIG. 2 is a schematic enlarged view of an area II of FIG. 1.

A channel of a TFT may be formed of the semiconductor layer (not illustrated). The semiconductor layer (not illustrated) may overlap the gate electrodes 224-1 and 224-2. The source electrodes 273-1 and 273-2 may be separated from FIG. 1 is a schematic exploded perspective view of an exemplary embodiment of an LCD 500. FIG. 2 is a schematic enlarged view of area II of FIG. 1.

Referring to FIGS. 1 and 2, the exemplary LCD 500 includes a first substrate 100, a second substrate 200 which is separated from the first substrate 100 and faces the first substrate 100, and a liquid crystal layer 300 which is disposed between the first substrate 100 and the second substrate 200.

Each of the first and second substrates 100 and 200 includes a display area DA and a non-display area NDA. The display area DA is an area in which an image is displayed, and the non-display area NDA is an area in which no image is displayed. The display area DA is surrounded by the non-display area NDA.

A common electrode 110 may be disposed between the first substrate 100 and the second substrate 200 and may be a patternless electrode without a slit pattern. A pixel electrode 291 may be disposed between the second substrate 200 the drain electrodes 275-1 and 275-2 with respect to the semiconductor layer (not illustrated), respectively.

A storage electrode line SL may include a stem line 231 extending substantially parallel to the gate lines GL and a plurality of branch lines 235 extending from the stem line 231. The storage electrode line SL can be omitted, and the shape and position of the storage electrode line SL can be changed variously.

The non-display area NDA may be a light-blocking area surrounding the display area DA. A driving unit (not illustrated) which provides a gate driving signal, a data driving signal, etc. to each pixel PX of the display area DA may be disposed in the non-display area NDA of the second substrate 200. The gate lines GL and the data lines DL may extend from the display area DA to the non-display area NDA so as to be electrically connected to the driving unit (not illustrated).

The first substrate 100 may be a counter substrate of the second substrate 200. The common electrode 110 may be disposed on the second substrate 200.

A color filter layer (not illustrated) may be formed in an area corresponding to each pixel PX of the display area DA and include a red color filter (R), a green color filter (G) and a blue color filter (B). The color filter layer (not illustrated) may be included in any one of the first substrate 100 and the second substrate 200. For example, if the first substrate 100 includes the color filter layer (not illustrated), it may have a structure in which a base substrate (not illustrated) made of glass or polymer, the color filter layer (not illustrated), and an overcoat layer (not illustrated) are stacked. The overcoat layer (not illustrated) may be a planarization layer which covers the color filter layer (not illustrated). In this case, the common electrode 110 may be disposed on the overcoat layer (not illustrated).

For example, if the second substrate 200 includes the color filter layer (not illustrated), it may have a color filter-on-array (COA) structure in which color filters are formed on a transparent insulating substrate having TFTs. For example, the color filter layer (not illustrated) may be disposed between the passivation layer (not illustrated) which covers the source electrodes 273-1 and 273-2 and the drain electrodes 275-1 and 275-2 and the organic layer (not illustrated).

A light-blocking pattern layer (not illustrated) may be disposed at the boundary of each color filter R, G or B. The light-blocking pattern layer (not illustrated) may be included in any one of the first substrate 100 and the second substrate 200. For example, the light-blocking pattern layer (not illustrated) may be a black matrix.

Figure 3:
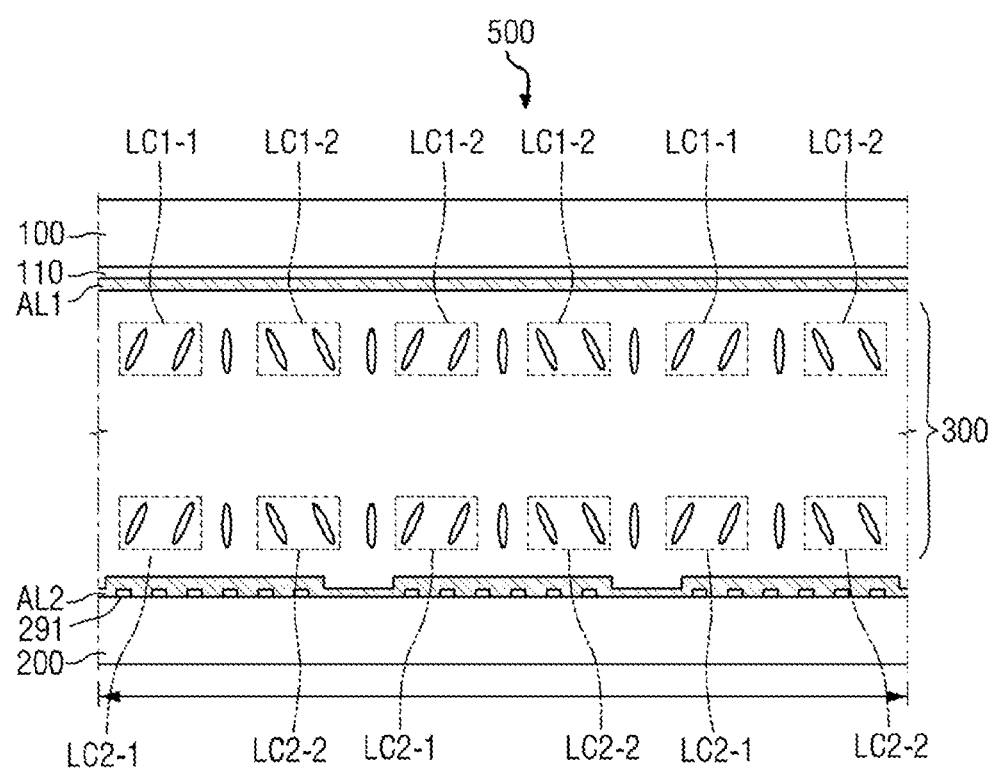
FIG. 3 is a schematic cross-sectional view taken along line of FIG. 1.

FIG. 3 is a schematic cross-sectional view taken along line of FIG. 1. The exemplary LCD 500 will now be described in greater detail with reference to FIG. 3. FIG. 3 schematically illustrates the alignment of liquid crystal molecules (LC1-1, LC1-2, LC2-1 and LC2-2) in an initial state in which the electric field is absent, i.e. no electric field has been applied to the LCD 500.

Referring to FIG. 3, first liquid crystal molecules LC1-1 and LC1-2 may be aligned on a surface of the first liquid crystal alignment layer AL1, and second liquid crystal molecules LC2-1 and LC2-2 may be aligned on a surface of the second liquid crystal alignment layer AL2. In addition, the first liquid crystal molecules LC1-1 and LC1-2 and the second liquid crystal molecules LC2-1 and LC2-2 may be arranged at a certain pretilt angle on the surface of the first liquid crystal alignment layer AL1 and the second liquid crystal alignment layer AL2, respectively.

In an example, in the initial state in which no electric field has been applied to the LCD 500, the $(1\text{-}1)^{th}$ liquid crystal molecules LC1-1 and $(1\text{-}2)^{th}$ liquid crystal molecules LC1-2 may form two or more domains having different alignment directions on the surface of the first liquid crystal alignment layer AL1. Likewise, the $(2\text{-}1)^{th}$ liquid crystal molecules LC2-1 and $(2\text{-}2)^{th}$ liquid crystal molecules LC2-2 may form two or more domains having different alignment directions on the surface of the second liquid crystal alignment layer AL2.

The alignment directions of the first liquid crystal molecules LC1-1 and LC1-2 in the domains formed by the first liquid crystal molecules LC1-1 and LC1-2 on the surface of the first liquid crystal alignment layer AL1 may correspond to those of the second liquid crystal molecules LC2-1 and LC2-2 in the domains formed by the second liquid crystal molecules LC2-1 and LC2-2 on the surface of the second liquid crystal alignment layer AL2. That is, the first liquid crystal molecules LC1-1 and LC1-2 and the second liquid crystal molecules LC2-1 and LC2-2 on the surface of the first liquid crystal alignment layer AL1 and the surface of the second liquid crystal layer AL2, may have the same pretilt direction along the same straight line.

More specifically, the $(1\text{-}1)^{th}$ liquid crystal molecules LC1-1 of the first alignment layer AL1 may be aligned in a first tilt direction, and the $(1\text{-}2)^{th}$ liquid crystal molecules LC1-2 of the first alignment layer AL1 may be aligned in a second tilt direction. The $(2\text{-}1)^{th}$ liquid crystal molecules LC2-1 of the second liquid crystal layer AL2 which are located at positions vertically corresponding to the $(1\text{-}1)^{th}$ liquid crystal molecules LC1-1 of the first liquid crystal alignment layer AL1 may be aligned in the first tilt direction, and the $(2\text{-}2)^{th}$ liquid crystal molecules LC2-2 which are located at positions vertically corresponding to the $(1\text{-}2)^{th}$ liquid crystal molecules LC1-2 of the first liquid crystal alignment layer AL1 may be aligned in the second tilt direction. The first tilt direction may be a direction at an angle of approximately $-\alpha$ degrees with respect to a virtual straight line perpendicular to the first liquid crystal alignment layer AL1 or the second liquid crystal alignment layer AL2, and the second tilt direction may be a direction at an angle of approximately $+\beta$ degrees with respect to the same virtual straight line. Here, $\beta$ is a positive real number.

At least one of the first liquid crystal alignment layer AL1 and the second liquid crystal alignment layer AL2 may include the reactive monomer of Formula 1. For example, both the first liquid crystal alignment layer AL1 and the second liquid crystal alignment layer AL2 may include the reactive monomer of Formula 1 below so as to cause the liquid crystal molecules LC1-1, LC1-2, LC2-1, and LC2-2 to be aligned vertically and to pretilt.

Formula 1

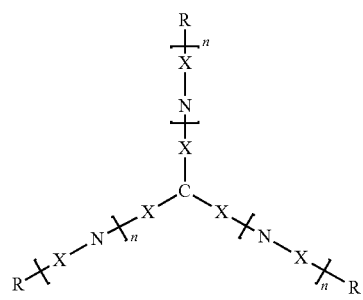

In Formula 1 n is 0 or 1; C is

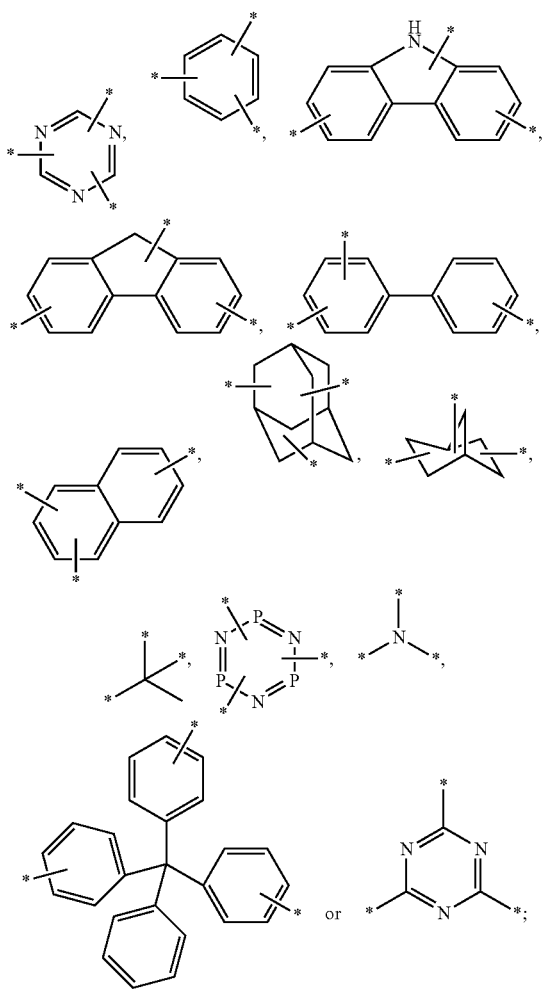

each X is independently ★—O—★,

or a bond; each N is independently

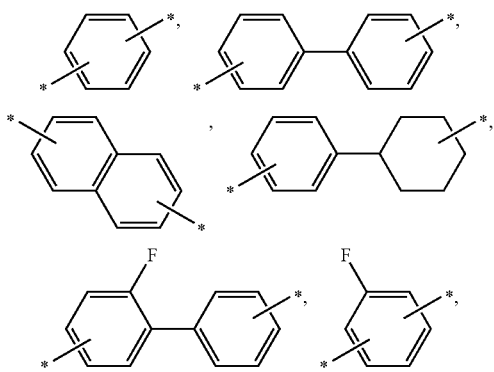

-continued

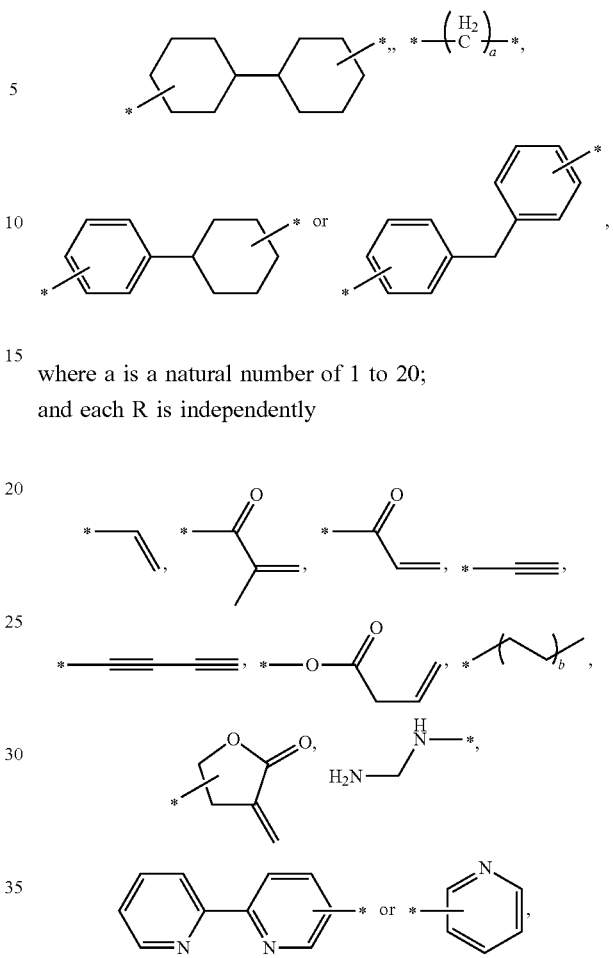

where a is a natural number of 1 to 20;
and each R is independently

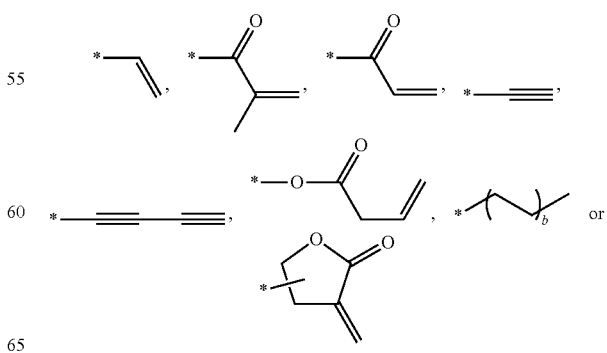

where b is a natural number of 1 to 20.

The reactive monomer may enable the liquid crystal molecules LC1-1, LC1-2, LC2-1, and LC2-2 located on the surface of the first liquid crystal alignment layer AL1 and the surface of the second liquid crystal alignment layer AL2 to be aligned vertically and to have a certain pretilt angle as described above.

In an exemplary embodiment, the reactive monomer of Formula 1 may include a mixture of reactive monomer A in which each R is independently and reactive monomer B in which each R is independently

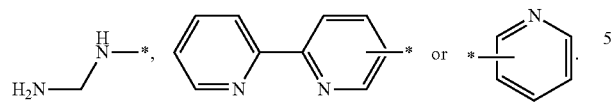

The reactive monomer A may polymerize on the first substrate 100 or the second substrate 200 to form the first and second liquid crystal alignment layers AL1 and AL2, and the reactive monomer B may cause the liquid crystal molecules LC1-1, LC1-2, LC2-1, and LC2-2 on the first liquid crystal alignment layer AL1 or the second liquid crystal alignment layer AL2 to be aligned vertically.

In addition, the reactive monomer of Formula 1 may be a single compound in which any one or two of R is

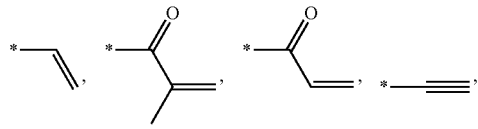

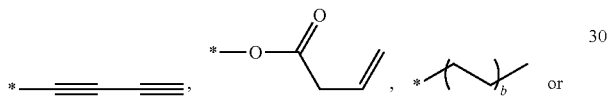

and the other one or two of R is

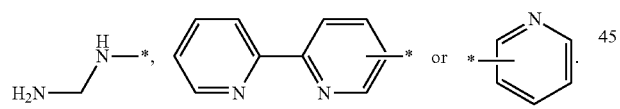

The R functional groups selected from

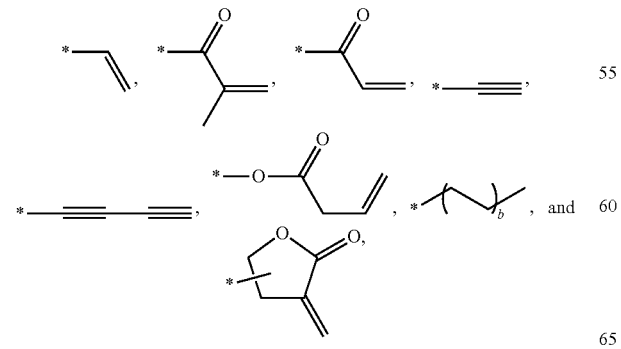

may help in the polymerization reaction for forming the first liquid crystal alignment layer AL1 or the second liquid crystal alignment layer AL2. The functional group R selected from

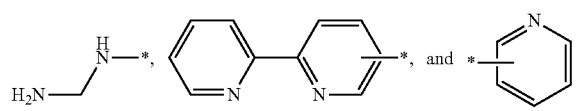

may cause the liquid crystal molecules LC1-1 and LC1-2 or LC2-1 and LC2-2 to be aligned vertically on the first liquid crystal alignment layer AL1 or the second liquid crystal alignment layer AL2.

More specifically, the reactive monomer of Formula 1 may be any one of Formulas 2 through 4 below:

Formula 2

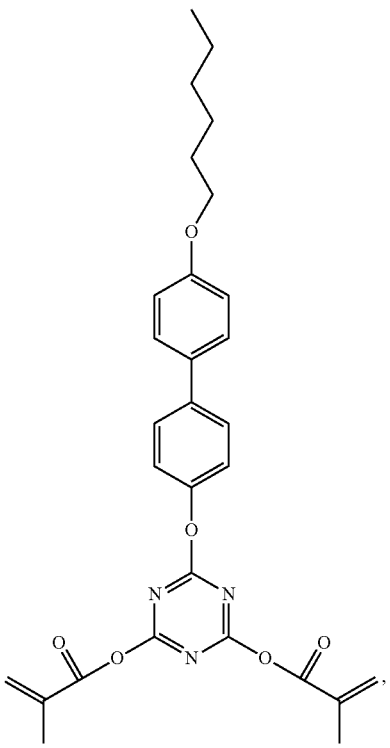

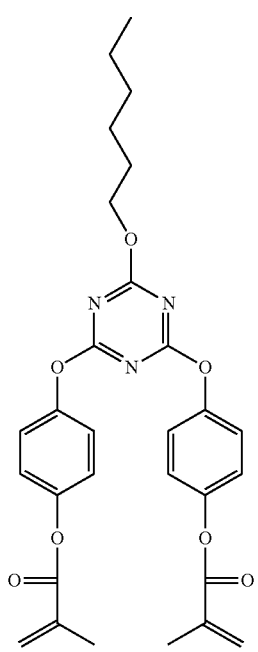

Formula 3

Formula 4

At least one of the first liquid crystal alignment layer AL1 and the second liquid crystal alignment layer AL2 may further include a polymerization initiator to facilitate the polymerization of the reactive monomer. Since the polymerization initiator is widely known to those of ordinary skill in the art, a detailed description thereof is omitted.

Disclosed herein also is a method of manufacturing the LCD 500. FIGS. 4 through 9 are schematic cross-sectional views illustrating an exemplary embodiment of a method of manufacturing the LCD 500.

Figure 4:
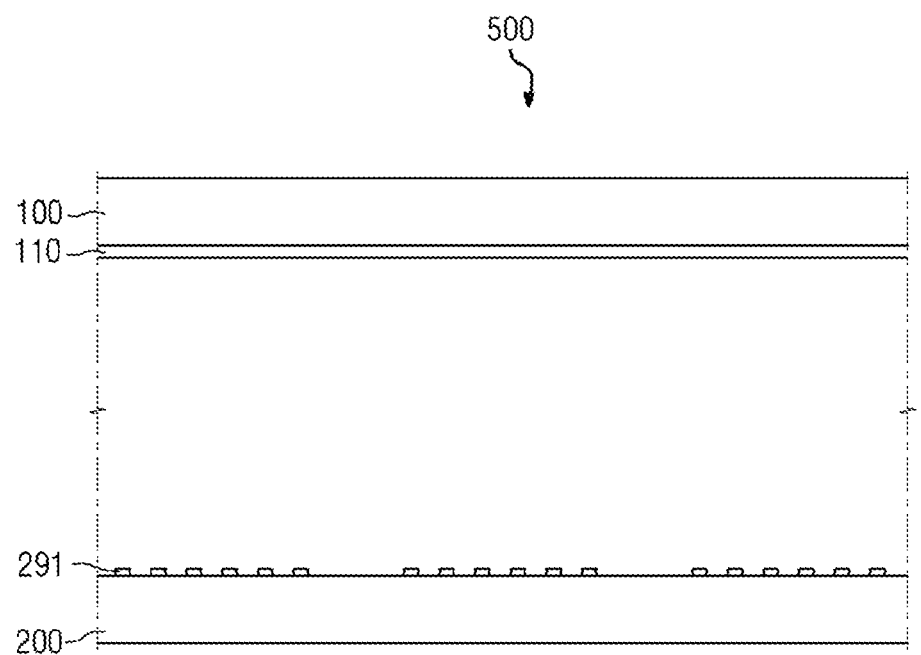
FIGS. 4 through 9 are schematic cross-sectional views illustrating an exemplary embodiment of a method of manufacturing an LCD.

Referring to FIG. 4, a first substrate 100 is placed to face a second substrate 200 with a predetermined cell gap maintained therebetween. For example, the second substrate 200 may be a TFT substrate, and the first substrate 100 may be a counter substrate of the second substrate 200 as well as a color filter substrate.

A common electrode 110 may be placed under the first substrate 100, that is, on a surface of the first substrate 100 which faces the second substrate 200. The common electrode 110 may be made of a material including at least one of indium tin oxide, indium zinc oxide, indium oxide, zinc oxide, tin oxide, gallium oxide, titanium oxide, aluminum, silver, platinum, chrome, molybdenum, tantalum, niobium, zinc, magnesium, any alloy thereof, and a stack thereof. The common electrode 110 may be a patternless electrode without a slit pattern.

A pixel electrode 291 may be placed on the second substrate 200 and may be made of a material including at least one of indium tin oxide, indium zinc oxide, indium oxide, zinc oxide, tin oxide, gallium oxide, titanium oxide, aluminum, silver, platinum, chrome, molybdenum, tantalum, niobium, zinc, magnesium, any alloy thereof, and a stack thereof. As described above, the pixel electrode 291 may be a patterned electrode having a slit pattern, and part of the second substrate 200 may be exposed through the slit pattern of the pixel electrode 291.

Figure 5:
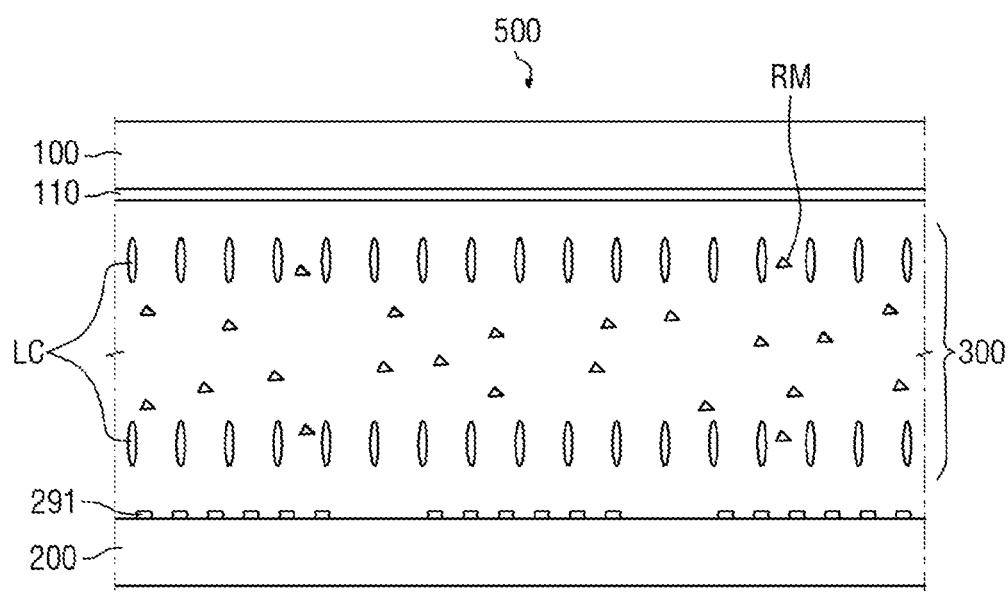

Referring to FIG. 5, a liquid crystal layer 300 is disposed between the first substrate 100 and the second substrate 200 which face each other. That is, liquid crystals are injected into a space between the first substrate 100 and the second substrate 200. The liquid crystal layer 300 may be formed by injecting or dropping a liquid crystal composition that contains liquid crystal molecules LC1, LC2 into the space between the first substrate 100 and the second substrate 200. The liquid crystal layer 300 may include the above-described alignment layer composition comprising the reactive monomer of Formula 1 in addition to the liquid crystal composition.

The liquid crystal composition may further contain a polymerization initiator to facilitate the polymerization reaction of the reactive monomer contained in a first liquid crystal alignment layer AL1 and a second liquid crystal alignment layer AL2.

Figure 6:
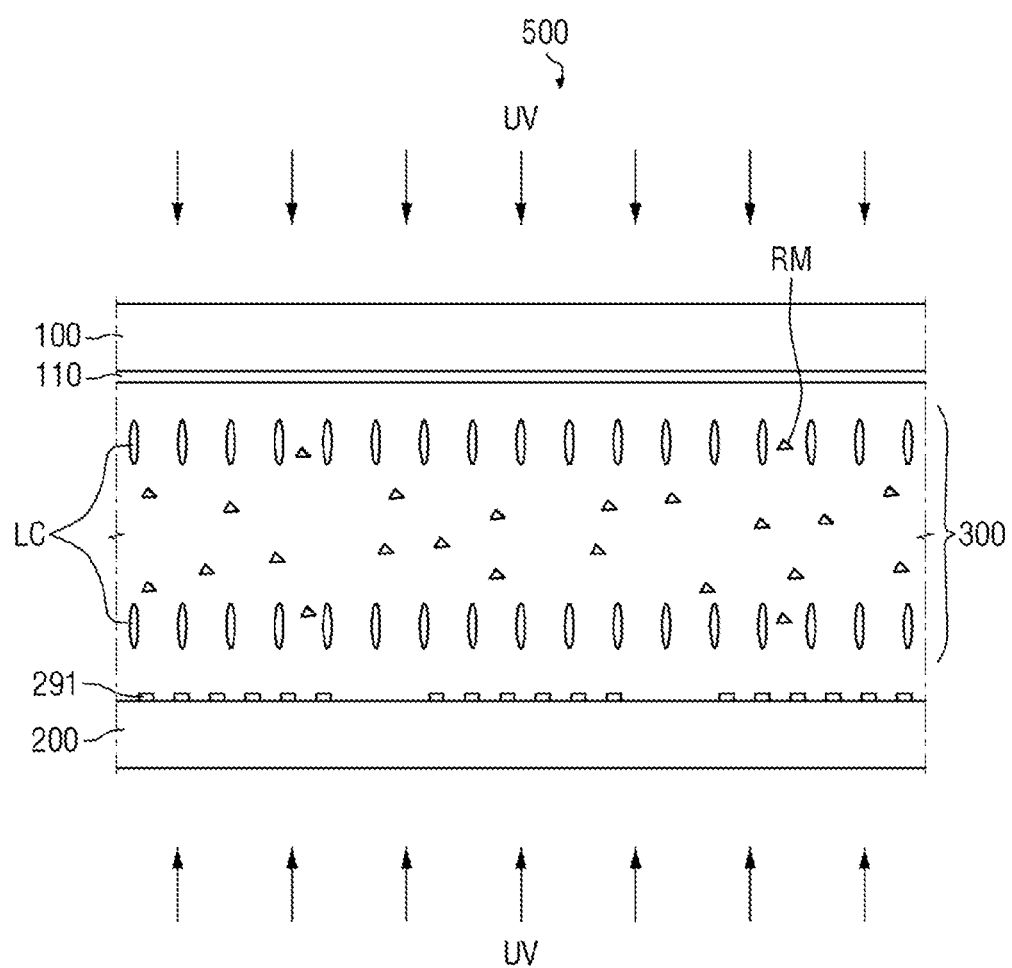
Figure 7:
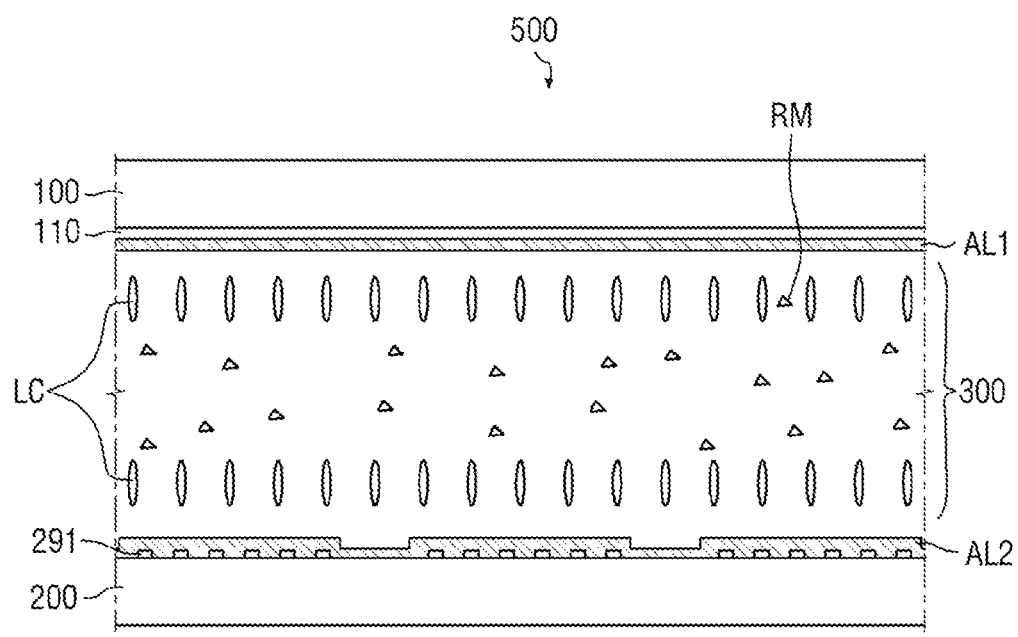

Referring to FIG. 6, ultraviolet (UV) light is irradiated toward at least any one of the first substrate 100 and the second substrate 200 in the absence of an electric field. In this process, a polymerization reaction of the reactive monomers RM included in the liquid crystal layer 300 may be initiated on a surface of the common electrode 110 which faces the second substrate 200, and on the first substrate 100 and the pixel electrode 291, thereby forming the first liquid crystal alignment layer AL1 and the second liquid crystal alignment layer AL2 as illustrated in FIG. 7. The liquid crystal layer 300 may also include the above-described polymerization initiator to facilitate the polymerization reaction.

The irradiating of the UV light in the absence of the electric field may initiate polymerization of the reactive monomers RM to form the first liquid crystal alignment layer AL1 and the second liquid crystal alignment layer AL2. The polymers of the reactive monomers RM may be shaped as protrusions. In addition, the irradiating of the UV light in the absence of the electric field may cause the liquid crystal composition on the first liquid crystal alignment layer AL1 and the second liquid crystal alignment layer AL2 to be aligned vertically.

More specifically, each liquid crystal molecule LC may have negative dielectric anisotropy. The liquid crystal molecules LC may be aligned substantially perpendicularly to the first substrate 100 and the second substrate 200 by the irradiating of the UV light to the LCD 500 in the absence of the electric field. Here, when the liquid crystal molecules LC are aligned substantially perpendicularly to the first substrate 100 and the second substrate 200, they may be aligned at an angle of, e.g., about 87.5 to less than about 90 degrees to the first substrate 100 and the second substrate 200.

The irradiating of the UV light in the absence of the electric field may cause some of the reactive monomers RM existing in the liquid crystal layer 300 to form the first liquid crystal alignment layer AL1 and the second liquid crystal alignment layer AL2. Accordingly, the reactive monomer content of the liquid crystal layer 300 may be reduced. It can be understood that the reduced amount of the reactive monomers RM corresponds to the amount of reactive monomer used to form the first liquid crystal alignment layer AL1 or the second liquid crystal alignment layer AL2.

Figure 8:
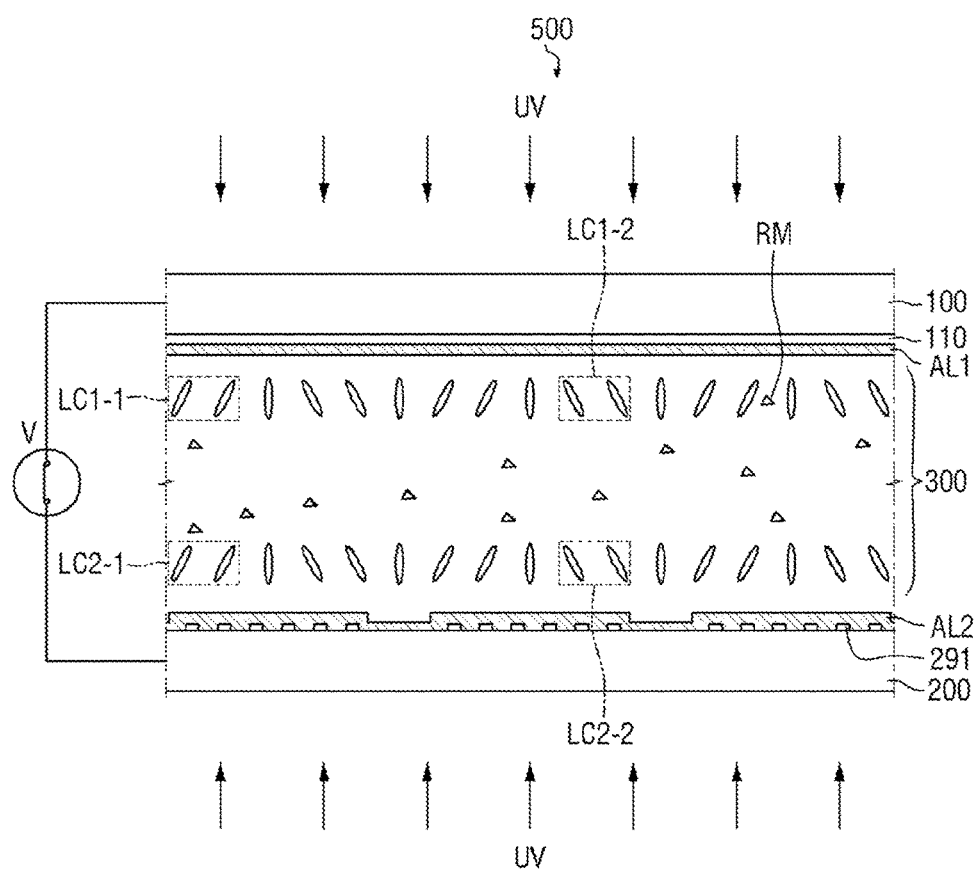

Referring to FIG. 8, when an electric field is applied to the LCD 500, the liquid crystal molecules LC1-1, LC1-2, LC2-1, and LC2-2 may tilt in a direction perpendicular to the electric field formed between the common electrode 110 and the pixel electrode 291. That is, the $(1-1)^{th}$ liquid crystal molecules LC1-1 and the $(2-1)^{th}$ liquid crystal molecules LC2-1 may be aligned in a first tilt direction, and the $(1-2)^{th}$ liquid crystal molecules LC1-2 and $(2-2)^{th}$ liquid crystal molecules LC2-2 may be aligned in a second tilt direction. Then, UV light is irradiated to the LCD 500 in the presence of the electric field. Accordingly, photopolymerization of the reactive monomers RM contained in the first liquid crystal alignment layer AL1 and the second liquid crystal alignment layer AL2 may be initiated, thus causing the $(1-1)^{th}$ liquid crystal molecules LC1-1 and the $(2-1)^{th}$ liquid crystal molecules LC2-1 to be aligned in the first tilt direction and the $(1-2)^{th}$ liquid crystal molecules LC1-2 and the $(2-2)^{th}$ liquid crystal molecules LC2-2 to be aligned in the second tilt direction.

The irradiating of the UV light in the presence of the electric field may cause the reactive monomer content of the liquid crystal layer 300 to be reduced further.

The first liquid crystal alignment layer AL1 or the second liquid crystal alignment layer AL2 may fix or stabilize the alignment direction of first liquid crystal molecules LC1-1, LC1-2 and the alignment direction of second liquid crystal molecules LC2-1, LC2-2. Therefore, the first liquid crystal molecules LC1-1, LC1-2 and the second liquid crystal molecules LC2-1, LC2-2 aligned on the surface of the first liquid crystal alignment layer AL1 or the second liquid crystal alignment layer AL2, may remain tilted even after the electric field applied to the LCD 500 is removed.

Figure 9:
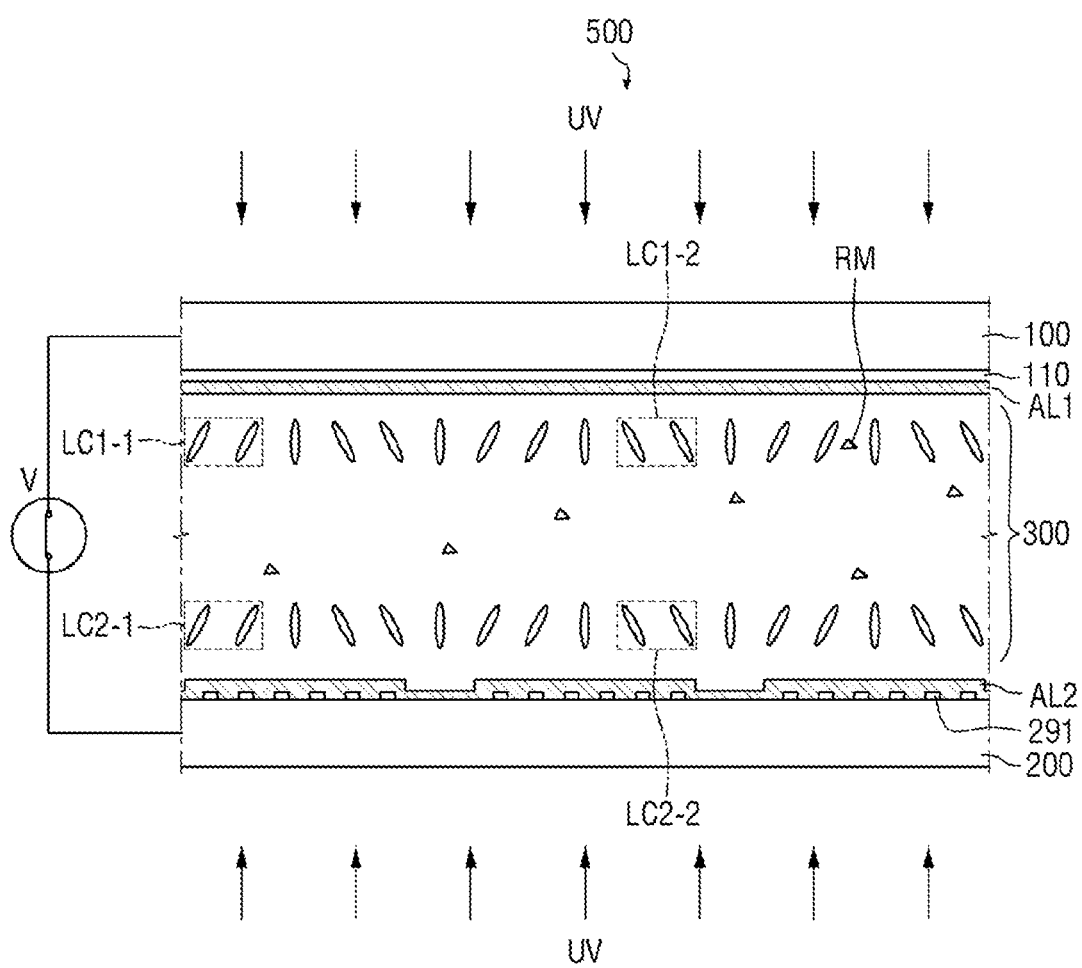

Referring to FIG. 9, in a state where no electric field has been applied to the LCD 500, the remaining reactive monomers RM may be removed by irradiating fluorescent UV light to the LCD 500. That is, the reactive monomers RM remaining in the liquid crystal layer 300 after failing to react in the irradiating of the UV light in the presence of the electric field can be removed.

In exemplary embodiments, an alignment layer composition can increase the vertical alignment of liquid crystals and cause the liquid crystals to pretilt easily.

In addition, in an LCD including the alignment layer composition, a liquid crystal layer can be easily aligned vertically and pretilted.

However, the effects of the present invention are not restricted to the one set forth herein. The above and other effects of the present invention will become more apparent to one of daily skill in the art to which the present invention pertains by referencing the claims.

What is claimed is:
1. An alignment layer composition comprising a reactive monomer represented by Formula 1 below:

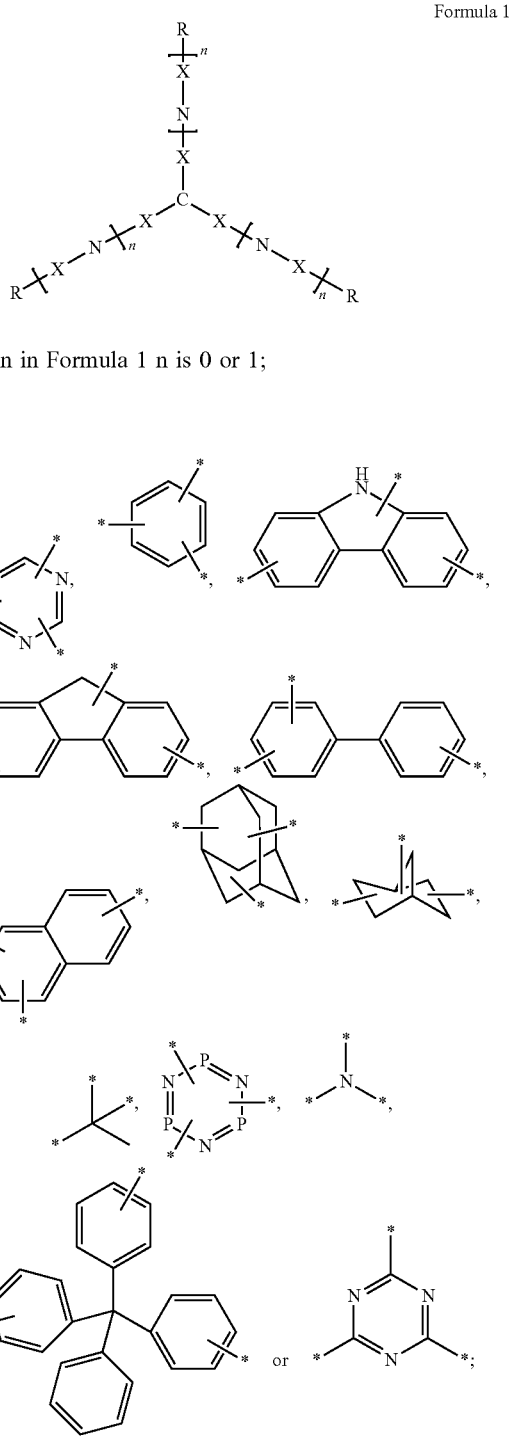

wherein in Formula 1 n is 0 or 1;
C is each X is independently

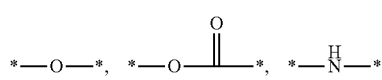

or a bond;

each N is independently

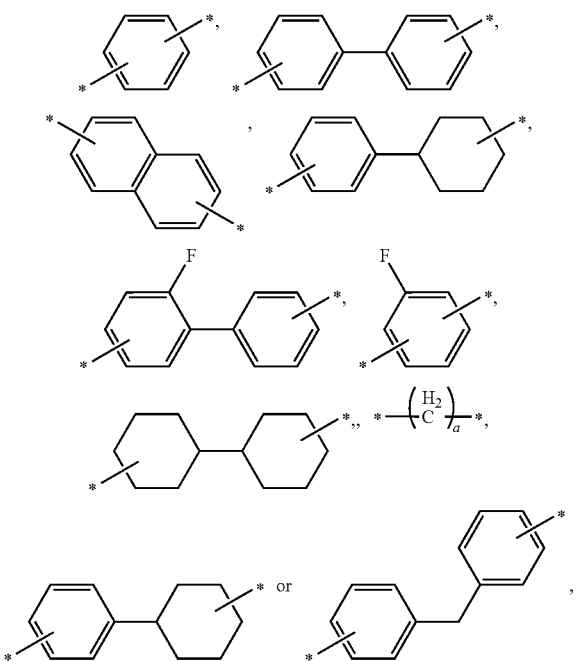

wherein a is a natural number of 1 to 20; and each R is independently

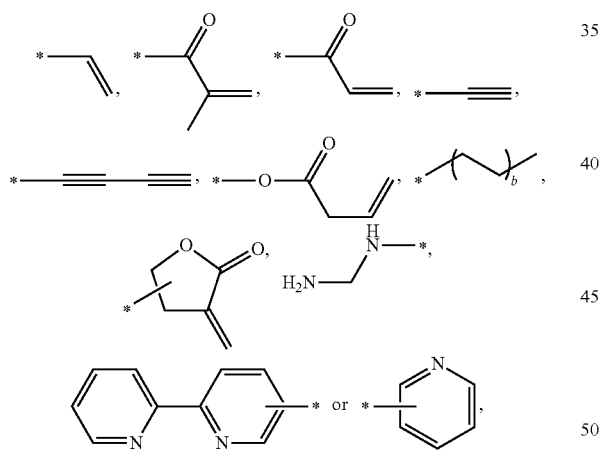

wherein b is a natural number of 1 to 20,
wherein the reactive monomer of Formula 1 comprises a mixture of reactive monomer A in which each R is independently

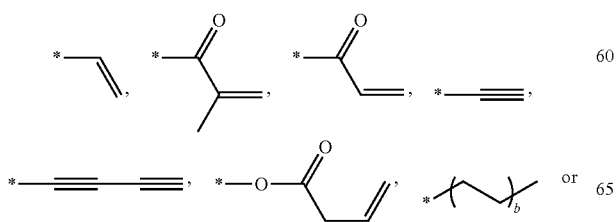

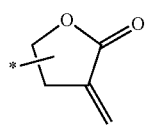

and reactive monomer B in which each R is independently

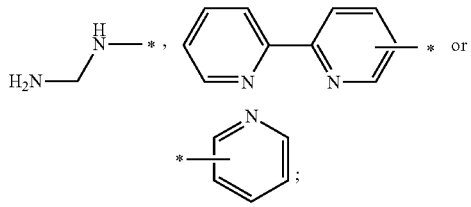

or
wherein in the reactive monomer of Formula 1, any one or two of R is

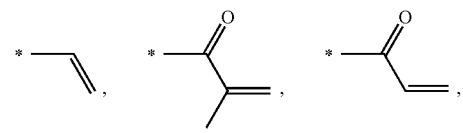

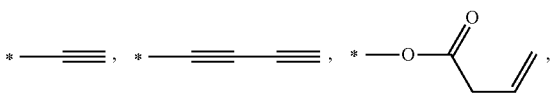

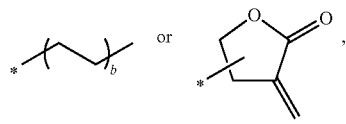

and the other one or two of R is

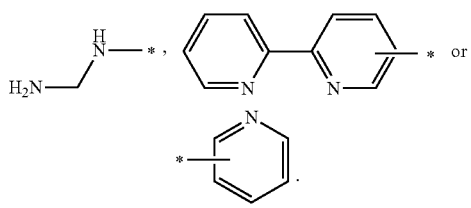

2. The alignment layer composition of claim 1, wherein the reactive monomer of Formula 1 is represented by Formula 2 below:

Formula 2

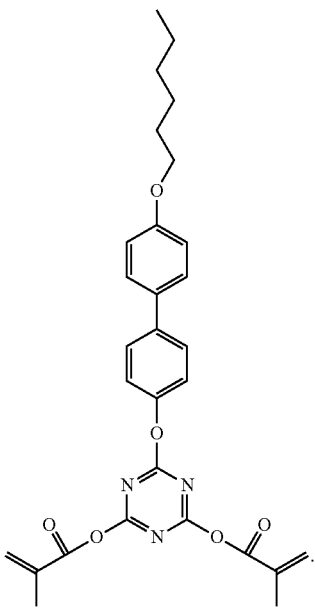

3. The alignment layer composition of claim 1, wherein the reactive monomer of Formula 1 is represented by Formula 3 below:

Formula 3

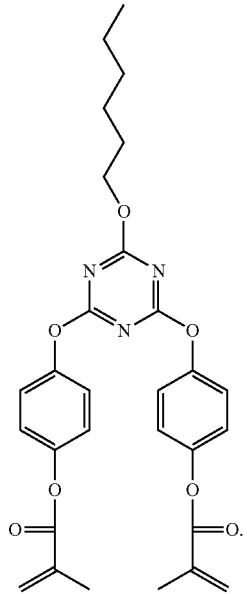

4. The alignment layer composition of claim 1, wherein the reactive monomer of Formula 1 is represented by Formula 4 below:

Formula 4

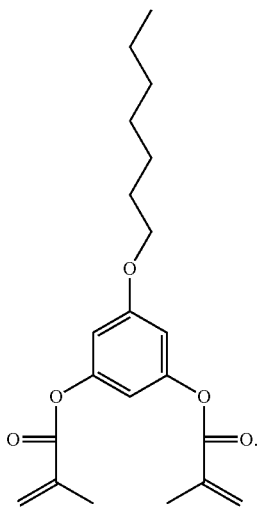

5. A liquid crystal display (LCD) comprising:
a first substrate;
a second substrate facing the first substrate;
a liquid crystal layer disposed between the first substrate and the second substrate;
a first liquid crystal alignment layer disposed between the liquid crystal layer and the first substrate; and
a second liquid crystal alignment layer disposed between the liquid crystal layer and the second substrate,
wherein at least one of the first liquid crystal alignment layer and the second liquid crystal alignment layer comprises a reactive monomer represented by Formula 1 below:

Formula 1

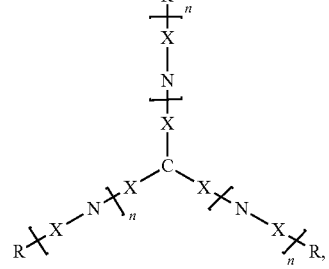

wherein in Formula 1 n is 0 or 1;
C is

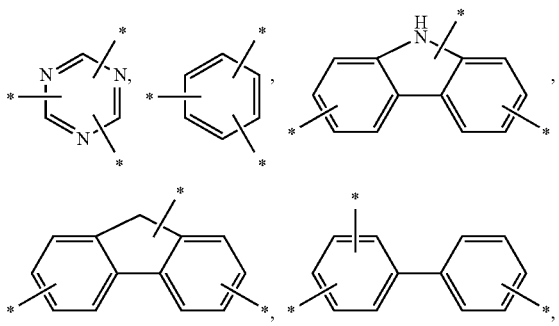

35
-continued

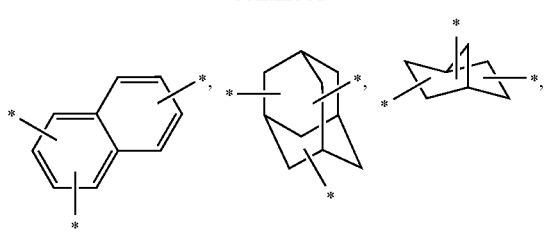

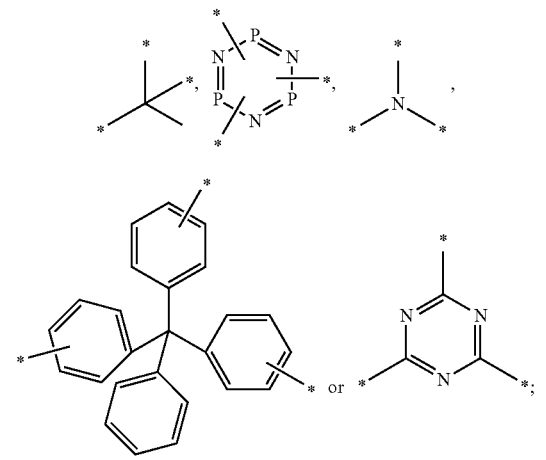

each X is independently ★—O—★,

or a bond;
each N is independently

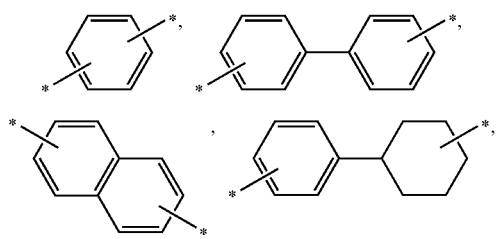

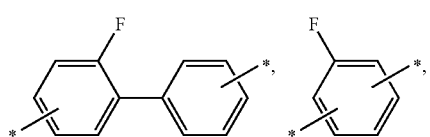

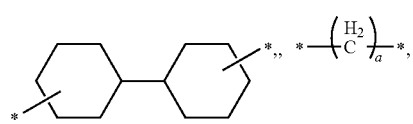

36
-continued

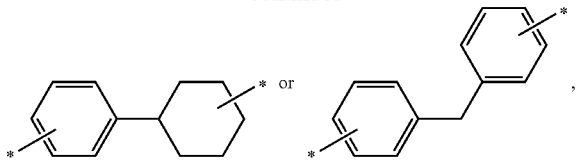

wherein a is a natural number of 1 to 20; and
each R is independently

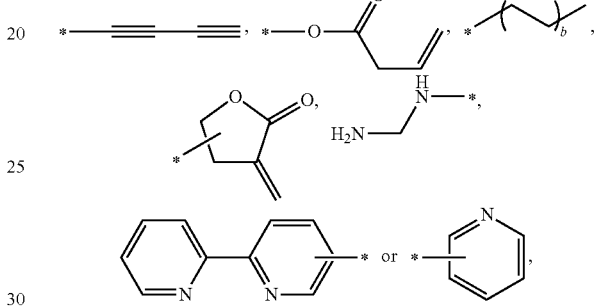

wherein b is a natural number of 1 to 20,
wherein the reactive monomer of Formula 1 comprises a mixture of reactive monomer A in which each R is independently

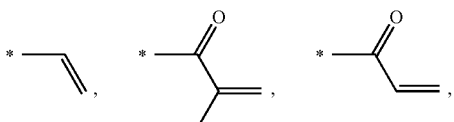

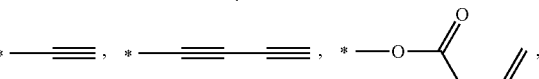

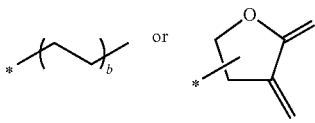

and reactive monomer B in which each R is independently

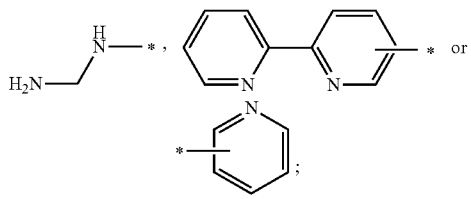

or
wherein in the reactive monomer of Formula 1, any one or two of R is

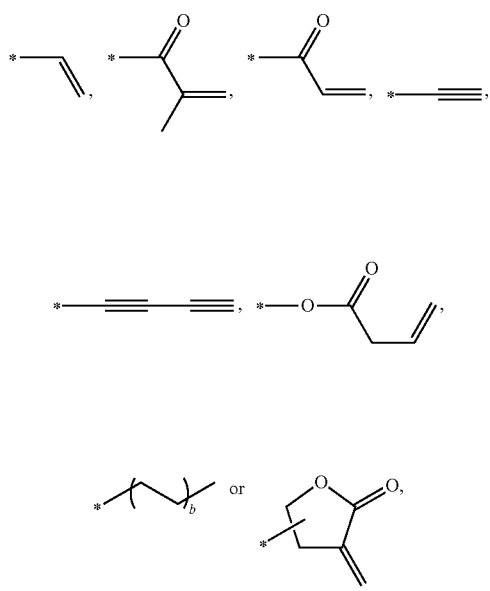

and the other one or two of R is

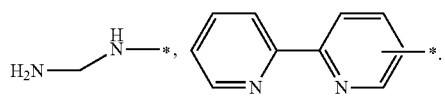

6. The LCD of claim 5, wherein the reactive monomer of Formula 1 is represented by Formula 2 below:

Formula 2

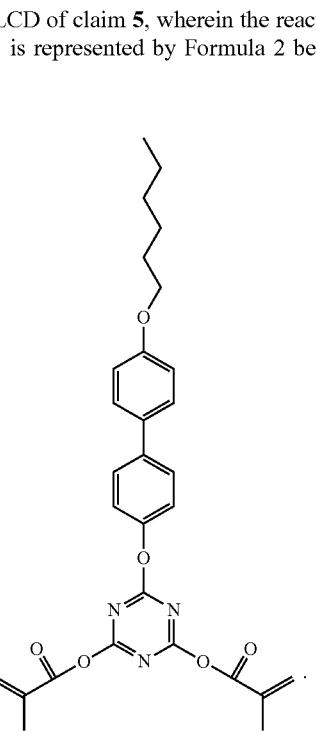

7. The LCD of claim 5, wherein the reactive monomer of Formula 1 is represented by Formula 3 below:

Formula 3

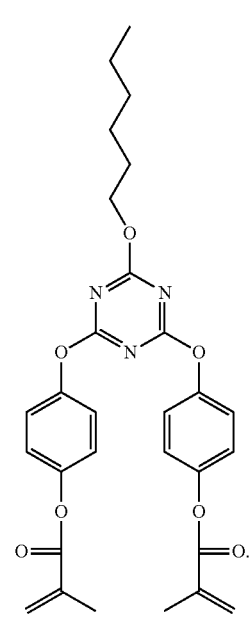

8. The LCD of claim 5, wherein the reactive monomer of Formula 1 is represented by Formula 4 below:

Formula 4

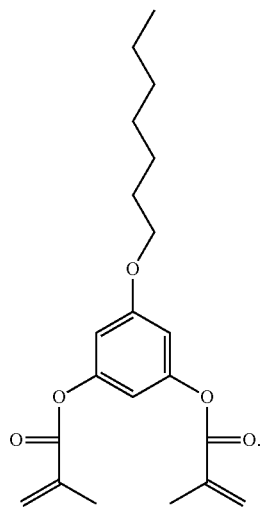

9. The LCD of claim 5, wherein both the first liquid crystal alignment layer and the second liquid crystal alignment layer comprise the reactive monomer of Formula 1.

10. A method of manufacturing an LCD, the method comprising:
preparing a first substrate and a second substrate facing each other;
injecting a liquid crystal composition into a space between the first substrate and the second substrate;
irradiating UV light toward at least one of the first substrate and the second substrate in the absence of an electric field; and
irradiating UV light toward at least one of the first substrate and the second substrate in the presence of the electric field, wherein the liquid crystal composition comprises an alignment layer composition comprising a reactive monomer represented by Formula 1 below:
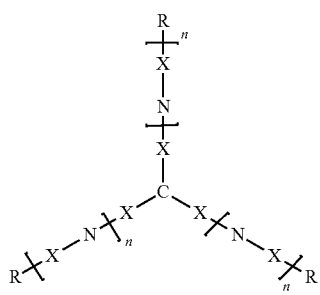
Formula 1
wherein in Formula 1 n is 0 or 1;
C is
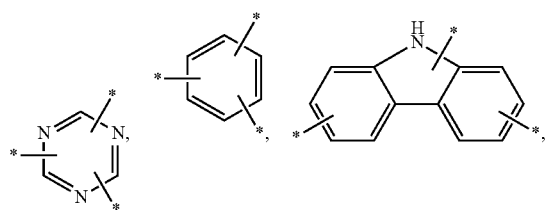
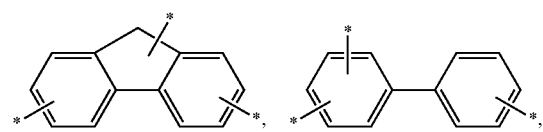
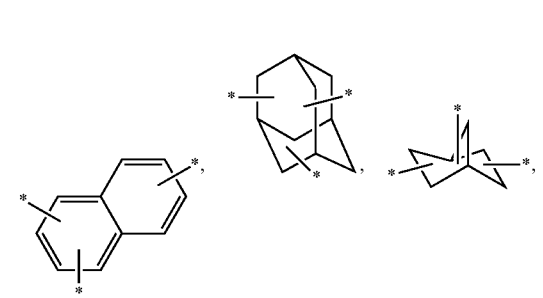
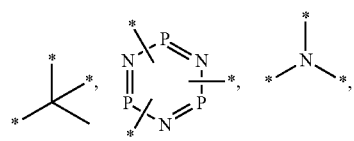
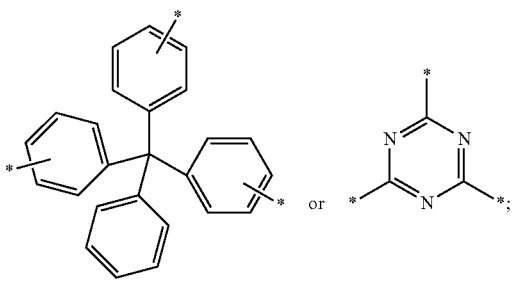
each X is independently ★—O—★,
or a bond;
each N is independently
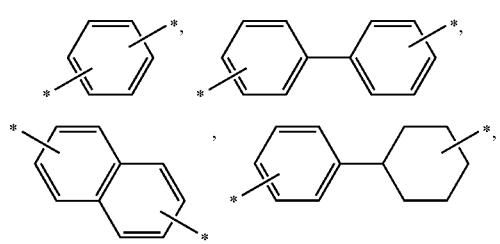
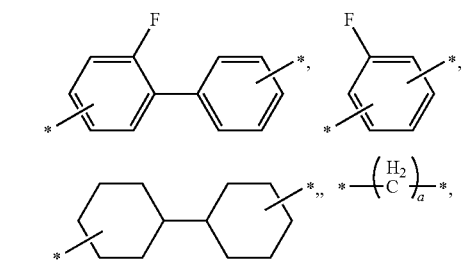
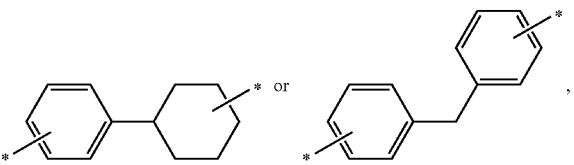
wherein a is a natural number of 1 to 20; and
each R is independently
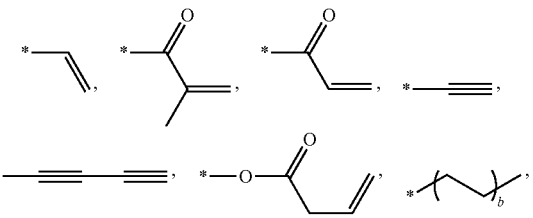

-continued

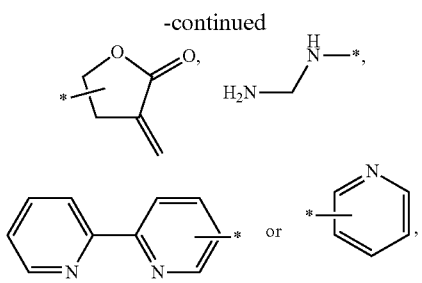

wherein b is a natural number of 1 to 20,
wherein the reactive monomer of Formula 1 comprises a mixture of reactive monomer A in which each R is independently

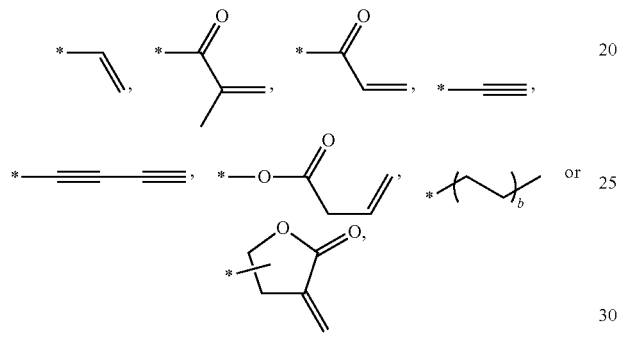

and reactive monomer B in which each R is independently

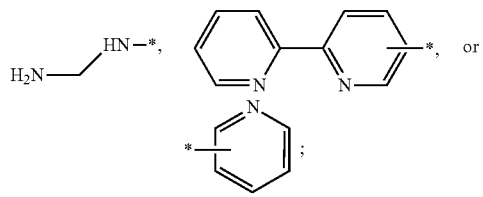

or
wherein the reactive monomer of Formula 1, any one or two of R is

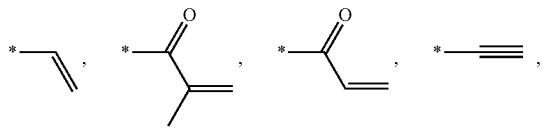

-continued

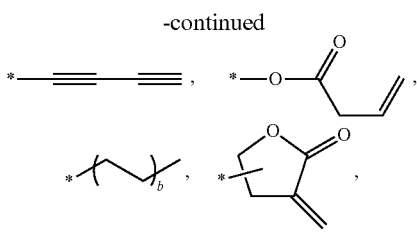

and the other one or two of R is

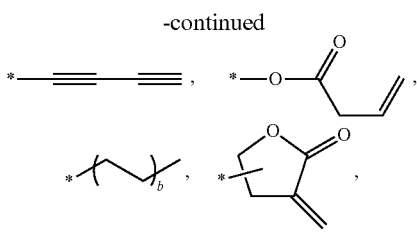

.

11. The method of claim 10, wherein the irradiating of the UV light in the absence of the electric field polymerizes the reactive monomer to form a first liquid crystal alignment layer on a surface of the first substrate which faces the second substrate and a second liquid crystal alignment layer on a surface of the second substrate which faces the first substrate.

12. The method of claim 11, wherein the injecting of the liquid crystal composition further comprises forming a liquid crystal layer comprising first liquid crystal molecules aligned on a surface of the first liquid crystal alignment layer and second liquid crystal molecules aligned on a surface of the second liquid crystal alignment layer, and the irradiating of the UV light in the absence of the electric field aligns the first liquid crystal molecules and the second liquid crystal molecules in a direction perpendicular to the first substrate or the second substrate, wherein the first liquid crystal molecules and the second liquid crystal molecules have negative dielectric anisotropy.

13. The method of claim 10, further comprising removing the electric field after the irradiating of the UV light in the presence of the electric field, wherein the first liquid crystal molecules and the second liquid crystal molecules are aligned at an angle relative to the first substrate or the second substrate after the irradiating of the UV light in the presence of the electric field.

14. The method of claim 11, wherein at least one of the first liquid crystal alignment layer and the second liquid crystal alignment layer is formed as a single layer of the polymerized reactive monomer of Formula 1.

15. The method of claim 10, further comprising irradiating UV light again after the irradiating of the UV light in the presence of the electric field.

* * * * *